US006852324B1

(12) United States Patent
Nabel et al.

(10) Patent No.: US 6,852,324 B1
(45) Date of Patent: Feb. 8, 2005

(54) IMMUNIZATION FOR EBOLA VIRUS INFECTION

(75) Inventors: Gary J. Nabel, Washington, DC (US); Anthony Sanchez, Atlanta, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/913,909

(22) PCT Filed: Dec. 23, 1998

(86) PCT No.: PCT/US98/27634

§ 371 (c)(1),
(2), (4) Date: Aug. 17, 2001

(87) PCT Pub. No.: WO99/32147

PCT Pub. Date: Jul. 1, 1999

Related U.S. Application Data

(60) Provisional application No. 60/068,655, filed on Dec. 23, 1997.

(51) Int. Cl.[7] ............................................. A61K 39/12

(52) U.S. Cl. ............................ 424/199.1; 424/204.1; 424/278.1; 435/320.1; 536/23.72

(58) Field of Search .......................... 424/199.1, 204.1, 424/209.1, 211.1, 224.1, 278.1; 435/320.1; 536/23.72

(56) References Cited

U.S. PATENT DOCUMENTS 6,197,568 B1    3/2001    Marks et al.

OTHER PUBLICATIONS

International Preliminary Examination Report from PCT/US98/27364, filed Dec. 23, 1998.
Palese et al. (1996) Negative–strand RNA viruses: Genetic engineering and applications. PNAS 93:11354–11358.
Sanchez et al. (1996) The virion glycoproteins of Ebola viruses are encoded in two reading frames and are expressed through transcriptional editing. PNAS 93:3602–3607.
Arai, H., et al., (1997) *Inhibition of the alloantibody response by DC95 ligand.* Nature Med. 3:843–848.
Border, W.A., et al., (1995) *Targeting TGF–β for treatment of disease.* Nature Med. 1:1000–1001.
Bowen, E.T.W., et al. (1977) *Viral heamorrhagic fever in southern Sudan and northern Zaire.* Lancet 1:571–573.
Bukreyev, A. A., et al. (1993) *The GP–protein of Marburg virus contains the region similar to the immunosuppressive domain' of oncogenic retrovirus P15E proteins.* FEBS. Lett. 323:183–187.
Cianciolo, G.J., et al. (1985) *Inhibition of lymphocyte proliferation by a synthetic peptide homologous to retroviral envelope proteins.* Science 230:453–455.

Clegg, J.C.S., et al. (1997) *Vaccines against arenaviruses and filoviruses.* New Generation Vaccines. (eds Levine, M.M., et al.) 749–765 (Marcel Dekker, New York).
Corr, M., et al., (1996) *Gene Vaccination with Naked Plasmid DNA: Mechanism of CTL priming.* J. Exp. Med. 184:1555–1560.
Davis, L.S., et al. (1995) *Measurement of human and murine interleukin 2 and interleukin 4.* Current Protocols in Immunology (eds. Collgan, J.E., et al. ) 6.3.1–6.3.12 (John Wiley & Sons, NY).
Doe, B., et al. (1996) *Induction of cytotoxic T lymphocytes by intramuscular immunization with plasmid DNA is facilitated by bone marrow–derived cells.* Proc. Natl., Acad. Sci. USA 93:8578–8583.
Doolan, D.L., et al. (1996) *Circumventing genetic restriction of protection against malaria with multigene DNA immunication: CD8 T Cell–, Interferon γ, and Nitric Oxide–Dependent immunity.* J. Exp. Med. 183:1739–1746.
Harris, D.T., et al. (1987) *Inhibition of human natural killer cell activity by a synthetic peptide homologous to a conserved region in the retroviral protein, p15E.* J. Immunol. 138:889–894. Iwasaki, A., et al. (1997) *The dominant role of bone marrow–derived cells in CTL Induction following plasmid DNA immunization at different sites.* J. Immunol. 159:11–14.
Iwasaki, A., et al. (1997) *The dominant role of bone marrow–derived cells in CTL induction following plasmid DNA immunization at different sites.* J. Immunol. 159:11–14.
Jahrling, P.B., et al. (1986) *Passive Immunization of Ebola virus–infected cynomologus monkeys with immunoglobulin from hyperimune horses.* Arch. Virol. Suppl. 11:135–140.
Jorgensen, J.L., et al. (1992) *Molecular components of T–cell recognition.* Annu. Rev. Immunol. 10:835–873.
Ksiazek T.G., et al. (1991) *Laboratory diagnosis of Biovirus infections in nonhuman primates.* Lab. Animal 20:334–46.
Ksiazek T.G., et al. (1992) *Enzyme immunosorbent assay for Ebola virus antigens in tissues of infected primates.* J. Clin. Microbiol. 30:947–950.
Manthrope, M., et al. (1993) *Gene therapy by intramuscular injection of plasmid DNA: Studies on firefly luciferase gene expression in mice.* Hum. Gene. Ther. 4:419–431.

(List continued on next page.)

Primary Examiner—Laurie Scheiner
(74) Attorney, Agent, or Firm—Knobbe, Martens, Olson & Bear, LLP

(57) ABSTRACT

Ebola virus vaccines comprising nucleic acid molecules encoding Ebola viral proteins are provided. In one embodiment, the nucleic acid molecule encodes the transmembrane form of the viral glycoprotein (GP). In another embodiment, the nucleic acid molecule encodes the secreted form of the viral glycoprotein (sGP). In yet another embodiment, the nucleic acid molecule encodes the viral nucleoprotein (NP). Methods for immunizing a subject against disease caused by infection with Ebola virus are also provided.

12 Claims, 12 Drawing Sheets

OTHER PUBLICATIONS

McCormick; J.B., et al. (1983) *Biologic differences between strains of Ebois virus from Zaire and Sudan.* J. Infect. Dis. 147:264–267.

Monaco, J.J. (1992) *A molecular model of MHC class-restricted antigen processing.* Immunol. Today 13:173–179.

Ohno, T., et al. (1997) *Combination gene transfer to potentiate tumor regression.* Gene Thera 4:361–368.

Peters, C.J., et al. (1994) *Fiolviruses as emerging pathogens.* Semin. Virol. 5:147–154.

Peters, C.J., et al. (1996) *Filovridae: Marburg and Ebola Viruses.* Fields Virology (eds. Fields, B.N., et al.) 1161–1176, Lippincott–Raven, Philadelphia.

Raz, E., et al. (1993) *Systemic immunological effects of cytokine genes injected into skeletal muscle.* Proc. Natl. Acad. Sci. USA 90:4523–4527.

Raz, E., et al. (1994) *Intradermal gene immunization: The possible role of DNA uptake in the induction of cellular Immunity to viruses.* Proc. Natl., Acad. Sci. USA, 91:9519–9523.

Sanchez, A., et al. (1989) *The Nucleoprotein gene of Ebola virus: Cloning, sequencing, and in Vitro expression.* Virology 170:81–91.

Sanchez, A., et al., (1993) *Sequence analysis of the Ebola virus genome: organization, genetic elements, and comparison with the genome of Marburg virus.* Virus. Res. 29:215–240.

Sanchez, A., et al. (1996) *The virion glycoproteins of Ebola viruses are encoded in two reading frames and are expressed through transcriptional editing.* Proc. Natl. Acad. Sci. USA, 93:3602–3607.

Sedegah, M., et al. (1994) *Protection against malaria by immunization with plasmid DNA encoding cirumsporozoite protein.* Proc. Natl. Acad. Sci, USA 91:9866–9870.Ksiazek, T.G. (1991) *Laboratory diagnosis of filovirus infections in nonhuman primates.* Lab. Animal 20:34–46.

Tan, B.T.G., et al. (1985) *Production of monoclonal antibodies defining guinea pig T-cell surface markers and a strain 13 la-like antigen: The value of immunohistological screening.* Hybridoma 4:115–124.

Tang, D.C., et al. (1992) *Genetic immunization is a single method for eliciting an immune response.* Nature 356:152–154.

Tascon, R.E., et al. (1996) *Vaccination against tuberculosis by DNA injection.* Nature Med. 2:888–892.

Ulmer, J.B., et al. (1993) *Heterologous protection against influenza by injection of DNA encoding a viral protein.* Science 259:1745–1749.

Volchkov, V.E., et al. (1992) *The envelope glycoprotein of Ebola virus contains an immunosuppressive-like domian similar to oncogenic retroviruses.* FEBS, Lett. 305:181–184.

Waisman, A., et al. (1996) *Suppressive vaccination with DNA encoding a variable region gene of the T-cell receptor prevents autoimmune encephalomyelitis and activates Th2 immunity.* Nature Med., 2:899–905.

Wolff, J.A., et al. (1990) *Direct gene transfer into mouse muscle in vivo.* Science 247:1465–1468.

Xu, L., et al. (1998) Immunization for Ebola virus infection. Nature Med. 4:37–42.

Zinkemagel, R.M., et al. (1997) *The discovery of MHC restriction.* Immunol. Today 18:14–17.

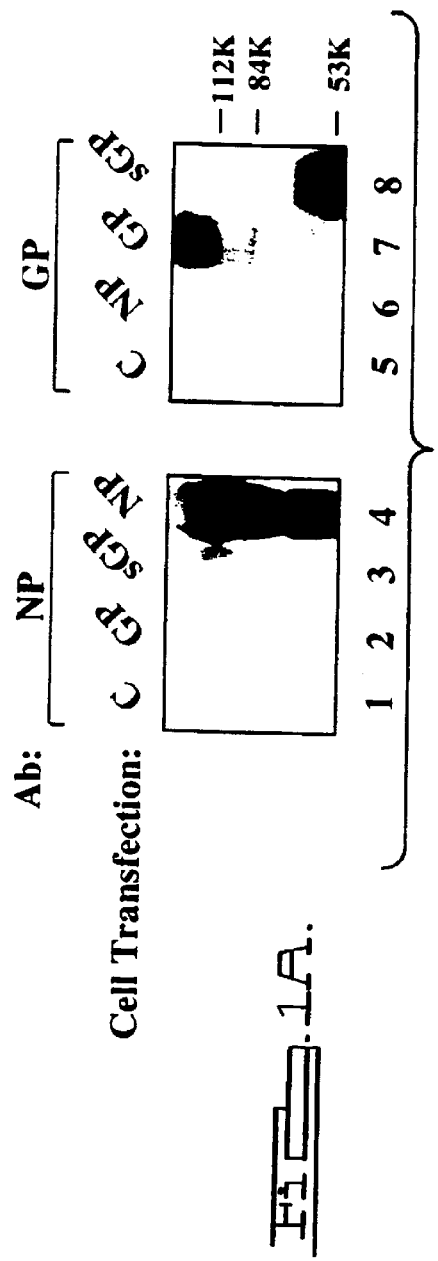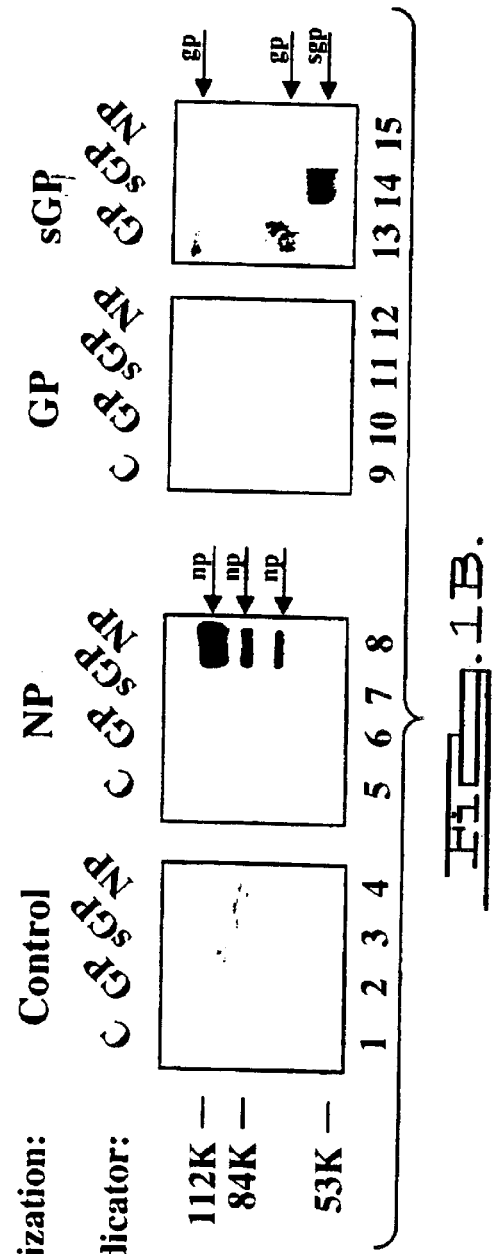

FIGURE 3C

Protected

Liver:

Lung:

Spleen:

Infected

Liver:

Lung:

Spleen:

SEQUENCE LISTING

```
<160> NUMBER OF SEQ ID NOS: 4

<210> SEQ ID NO 1
<211> LENGTH: 7003
<212> TYPE: DNA
<213> ORGANISM: Artificial Sequence
<220> FEATURE:
<223> OTHER INFORMATION: Description of Artificial Sequence:Plasmid
      containing DNA forGP of Ebola Virus, Ivory Coast
      strain
<221> NAME/KEY: 5'UTR
<222> LOCATION: (886)..(1129)
<223> OTHER INFORMATION: CMV IE 5' UT
<221> NAME/KEY: intron
<222> LOCATION: (1130)..(1840)
<223> OTHER INFORMATION: CMV IE INT
<221> NAME/KEY: enhancer
<222> LOCATION: (248)..(885)
<223> OTHER INFORMATION: CMV Enhancer
<221> NAME/KEY: gene
<222> LOCATION: (1870)..(4019)
<223> OTHER INFORMATION: GP(IC)
<221> NAME/KEY: gene
<222> LOCATION: (4020)..(4572)
<223> OTHER INFORMATION: TbGH
<221> NAME/KEY: gene
<222> LOCATION: (6068)..(6690)
<223> OTHER INFORMATION: Kan r
```

-continued

<400> SEQUENCE: 1

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca cgacccccgc ccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgcccccta ttgacgtcaa     600
tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg cggccgggaa cggtgcattg gaacgcggat    1020
tccccgtgcc aagagtgacg taagtaccgc ctatagactc tataggcaca ccctttggc     1080
tcttatgcat gctatactgt ttttggcttg gggcctatac cccccgctt ccttatgcta     1140
taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tattttttaca   1320
ggatggggtc ccatttatta tttacaaatt cacatataca acaacgccgt cccccgtgcc    1380
cgcagttttt attaaacata gcgtgggatc tccacgcgaa tctcgggtac gtgttccgga    1440
catggctct tctccggtag cggcggagct tccacatccg agccctggtc ccatgcctcc     1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgcgcggcc gctctagaat    1920
tctctaatca cagtcatcat gggagcgtca gggattctgc aattgccccg tgagcgcttc    1980
aggaaaacat cttcttgt ttgggtaata atcctattcc ataaagtctt ttcaatcccg      2040
ttggggttg tacacaacaa taccctacaa gtgagtgata ttgacaagtt tgtgtgccga    2100
gacaaactct cttcaactag ccaattgaag tcagtcgggt tgaacttgga gggcaatgga    2160
gtagcaactg atgtaccaac ggcaaccaaa agatggggtt ttcgagctgg tgttccacca    2220
aaggtggtaa attacgaagc tggagaatgg gctgagaact gttataacct ggctataaag    2280
```

-continued

```
aaagttgatg gtagtgagtg cctaccagaa gccctgagg gagtgaggga ttttccccgt   2340
tgccgctatg tacacaaagt ctcaggaact ggaccatgcc caggaggact cgcctttcac   2400
aaagaaggag ccttcttcct gtatgaccga ctcgcatcaa caatcattta tcggggtaca   2460
acctttgccg aaggagttat tgcatttctg atcttgccta aggcgcgaaa ggattttttc   2520
cagtctcctc cattgcatga gcctgccaac atgaccacgg atccctccag ttactatcac   2580
acgacaacaa taaactacgt ggttgataat tttggaacca acaccacaga gtttctgttc   2640
caagtcgatc atttgacgta tgtgcagctc gaggcaagat tcacaccaca attccttgtc   2700
ctcctaaatg aaaccatcta ctctgataac cgcagaagta acacaacagg aaaactaatc   2760
tggaaaataa atcccactgt tgataccagc atgggtgagt gggctttctg ggaaaataaa   2820
aaaacttcac aaaaacccct tcaagtgaag agttgtcttt cgtacctgta ccagaaaccc   2880
agaaccaggt ccttgacacg acagcgacgg tctctcctcc catctccgcc cacaaccacg   2940
caggcgaaga ccacaaagaa ttggtttcag aggattccac tccagtggtt cagatgcaaa   3000
acatcaaggg aaggacaca atgccaacca cagtgacggg tgtaccaaca accacaccct    3060
ctccatttcc aatcaatgct cgcaacactg atcataccaa atcatttatc ggcctggagg   3120
ggccccaaga agaccacagc accacacagc ctgccaagac caccagccaa ccaaccaaca   3180
gcacagaatc gacgacacta aacccaacat cagagccctc cagtagaggc acgggaccat   3240
ccagccccac ggtccccaac accacagaaa gccacgccga acttggcaag acaaccccaa   3300
ccacactccc agaacagcac actgccgcca gtgccattcc aagagccgtg caccccgacg   3360
aactcagtgg acctggcttc ctgacgaaca caatacgggg ggtgacaaat ctcctgacag   3420
gatccagaag aaagcgaagg gatgtcactc ccaatacaca acccaaatgc aacccaaacc   3480
tgcactattg gacagccttg gatgagggtg ctgccatagg tttagcctgg ataccatact   3540
tcgggccagc agctgaggga atttacactg aaggcataat ggagaatcaa aatggattga   3600
tctgtggatt gaggcagctg gccaacgaaa cgacacaagc tcttcaattg ttcttaaggg   3660
caactactga gttgcgtaca ttctctatac taaatcggaa agcaatagac ttcttgctcc   3720
aaagatgggg aggaacatgt cacattctag ggcctgattg ttgcattgaa ccccaagatt   3780
ggaccaaaaa tatcactgat aaaattgatc aaataatcca tgactttgtc gataataatc   3840
ttccaaatca gaatgatggc agcaactggt ggactggatg gaaacaatgg gttcctgctg   3900
gaataggaat cacaggagta atcattgcta ttattgcttt gctgtgcatt tgcaaattca   3960
tgctttgaac taatatagca tcatacttta gaattctaga ccaggcgcct ggatccagat   4020
ctgctgtgcc ttctagttgc cagccatctg ttgtttgccc ctccccgtg ccttccttga    4080 ccctggaagg tgccactccc actgtccttt cctaataaaa tgaggaaatt gcatcgcatt   4140
gtctgagtag gtgtcattct attctggggg gtggggtggg gcagcacagc aaggggagg    4200 attgggaaga caatagcagg catgctgggg atgcggtggg ctctatgggt acccaggtgc   4260
tgaagaattg acccggttcc tcctgggcca gaaagaagca ggcacatccc cttctctgtg   4320
acacaccctg tccacgcccc tggttcttag ttccagcccc actcatagga cactcatagc   4380
tcaggagggc tccgccttca atcccacccg ctaaagtact ggagcggtc tctccctccc    4440 tcatcagccc accaaaccaa acctagcctc caagagtggg aagaaattaa agcaagatag   4500
gctattaagt gcagagggag agaaaatgcc tccaacatgt gaggaagtaa tgagagaaat   4560
catagaattt cttccgcttc ctcgctcact gactcgctgc gctcggtcgt tcggctgcgg   4620
cgagcggtat cagctcactc aaaggcggta atacggttat ccacagaatc agggataac    4680
```

-continued

```
gcaggaaaga acatgtgagc aaaaggccag caaaaggcca ggaaccgtaa aaaggccgcg    4740
ttgctggcgt ttttccatag gctccgcccc cctgacgagc atcacaaaaa tcgacgctca    4800
agtcagaggt ggcgaaaccc gacaggacta taaagatacc aggcgtttcc ccctggaagc    4860
tccctcgtgc gctctcctgt tccgaccctg ccgcttaccg gatacctgtc cgcctttctc    4920
ccttcgggaa gcgtggcgct ttctcaatgc tcacgctgta ggtatctcag ttcggtgtag    4980
gtcgttcgct ccaagctggg ctgtgtgcac gaaccccccg ttcagcccga ccgctgcgcc    5040
ttatccggta actatcgtct tgagtccaac ccggtaagac acgacttatc gccactggca    5100
gcagccactg gtaacaggat tagcagagcg aggtatgtag gcggtgctac agagttcttg    5160
aagtggtggc ctaactacgg ctacactaga aggacagtat ttggtatctg cgctctgctg    5220
aagccagtta ccttcggaaa aagagttggt agctcttgat ccggcaaaca accaccgct    5280
ggtagcggtg ttttttttgt ttgcaagcag cagattacgc gcagaaaaaa aggatctcaa    5340
gaagatcctt tgatcttttc tacggggtct gacgctcagt ggaacgaaaa ctcacgttaa    5400
gggattttgg tcatgagatt atcaaaaagg atcttcacct agatcctttt aaattaaaaa    5460
tgaagtttta aatcaatcta agtatatat gagtaaactt ggtctgacag ttaccaatgc    5520
ttaatcagtg aggcacctat ctcagcgatc tgtctatttc gttcatccat agttgcctga    5580
ctccggggg ggggggcgct gaggtctgcc tcgtgaagaa ggtgttgctg actcatacca    5640
ggcctgaatc gccccatcat ccagccagaa agtgagggag ccacggttga tgagagcttt    5700
gttgtaggtg gaccagttgg tgattttgaa cttttgcttt gccacggaac ggtctgcgtt    5760
gtcgggaaga tgcgtgatct gatccttcaa ctcagcaaaa gttcgattta ttcaacaaag    5820
ccgccgtccc gtcaagtcag cgtaatgctc tgccagtgtt acaaccaatt aaccaattct    5880
gattagaaaa actcatcgag catcaaatga aactgcaatt tattcatatc aggattatca    5940
ataccatatt tttgaaaaag ccgtttctgt aatgaaggag aaaactcacc gaggcagttc    6000
cataggatgg caagatcctg gtatcggtct gcgattccga ctcgtccaac atcaatacaa    6060
cctattaatt tcccctcgtc aaaaataagg ttatcaagtg agaaatcacc atgagtgacg    6120
actgaatccg gtgagaatgg caaaagctta tgcatttctt tccagacttg ttcaacaggc    6180
cagccattac gctcgtcatc aaaatcactc gcatcaacca aaccgttatt cattcgtgat    6240
tgcgcctgag cgagacgaaa tacgcgatcg ctgttaaaag gacaattaca acaggaatc    6300
gaatgcaacc ggcgcaggaa cactgccagc gcatcaacaa tattttcacc tgaatcagga    6360
tattcttcta atacctggaa tgctgttttc ccggggatcg cagtggtgag taaccatgca    6420
tcatcaggag tacggataaa atgcttgatg gtcggaagag gcataaattc cgtcagccag    6480
tttagtctga ccatctcatc tgtaacatca ttggcaacgc taccttttgcc atgtttcaga    6540
aacaactctg gcgcatcggg cttcccatac aatcgataga ttgtcgcacc tgattgcccg    6600
acattatcgc gagcccattt atacccatat aaatcagcat ccatgttgga atttaatcgc    6660
ggcctcgagc aagacgtttc ccgttgaata tggctcataa cacccccttgt attactgttt    6720
atgtaagcag acagttttat tgttcatgat gatatatttt tatcttgtgc aatgtaacat    6780
cagagatttt gagacacaac gtggctttcc cccccccccc attattgaag catttatcag    6840
ggttattgtc tcatgagcgg atacatattt gaatgtattt agaaaaataa acaaataggg    6900
gttccgcgca catttccccg aaaagtgcca cctgacgtct aagaaaccat tattatcatg    6960
acattaacct ataaaaatag gcgtatcacg aggccctttc gtc    7003
```

```
<210> SEQ ID NO 2
<211> LENGTH: 7073
<212> TYPE: DNA
<213> ORGANISM: Artificial Sequence
<220> FEATURE:
<223> OTHER INFORMATION: Description of Artificial Sequence:Plasmid
      containing DNA for GP of Ebola Virus, Sudan strain
<221> NAME/KEY: 5'UTR
<222> LOCATION: (886)..(1129)
<223> OTHER INFORMATION: CMV IE 5' UT
<221> NAME/KEY: intron
<222> LOCATION: (1130)..(1840)
<223> OTHER INFORMATION: CMV IE INT
<221> NAME/KEY: enhancer
<222> LOCATION: (248)..(885)
<223> OTHER INFORMATION: CMV enhancer
<221> NAME/KEY: gene
<222> LOCATION: (1870)..(4089)
<223> OTHER INFORMATION: GP(S)
<221> NAME/KEY: gene
<222> LOCATION: (4090)..(4642)
<223> OTHER INFORMATION: TbGH
<221> NAME/KEY: gene
<222> LOCATION: (6138)..(6760)
<223> OTHER INFORMATION: Kan r

<400> SEQUENCE: 2
tcgcgcgttt cggtgatgac ggtgaaaacc tctgacacat gcagctcccg gagacggtca    60
cagcttgtct gtaagcggat gccgggagca gacaagcccg tcagggcgcg tcagcgggtg   120
ttggcgggtg tcgggctgg  cttaactatg cggcatcaga gcagattgta ctgagagtgc   180
accatatgcg gtgtgaaata ccgcacagat gcgtaaggag aaaataccgc atcagattgg   240
ctattggcca ttgcatacgt tgtatccata tcataatatg tacatttata ttggctcatg   300
tccaacatta ccgccatgtt gacattgatt attgactagt tattaatagt aatcaattac   360
ggggtcatta gttcatagcc catatatgga gttccgcgtt acataactta cggtaaatgg   420
cccgcctggc tgaccgccca acgacccccg cccattgacg tcaataatga cgtatgttcc   480
catagtaacg ccaataggga ctttccattg acgtcaatgg gtggagtatt tacggtaaac   540
tgcccacttg gcagtacatc aagtgtatca tatgccaagt acgccccta  ttgacgtcaa   600 tgacggtaaa tggcccgcct ggcattatgc ccagtacatg accttatggg actttcctac   660
ttggcagtac atctacgtat tagtcatcgc tattaccatg gtgatgcggt tttggcagta   720
catcaatggg cgtggatagc ggtttgactc acggggattt ccaagtctcc accccattga   780
cgtcaatggg agtttgtttt ggcaccaaaa tcaacgggac tttccaaaat gtcgtaacaa   840
ctccgcccca ttgacgcaaa tgggcggtag gcgtgtacgg tgggaggtct atataagcag   900
agctcgttta gtgaaccgtc agatcgcctg gagacgccat ccacgctgtt ttgacctcca   960
tagaagacac cgggaccgat ccagcctccg cggccgggaa cggtgcattg gaacgcggat  1020
tccccgtgcc aagagtgacg taagtaccgc ctatagactc tataggcaca ccctttggc   1080 tcttatgcat gctatactgt ttttggcttg gggcctatac accccgctt  ccttatgcta  1140 taggtgatgg tatagcttag cctataggtg tgggttattg accattattg accactcccc  1200
tattggtgac gatactttcc attactaatc cataacatgg ctctttgcca caactatctc  1260
tattggctat atgccaatac tctgtccttc agagactgac acggactctg tatttttaca  1320
ggatggggtc ccatttatta tttacaaatt cacatataca acaacgccgt cccccgtgcc  1380
cgcagttttt attaaacata gcgtgggatc tccacgcgaa tctcgggtac gtgttccgga  1440
catgggctct tctccggtag cggcggagct tccacatccg agccctggtc ccatgcctcc  1500
```

```
agcggctcat ggtcgctcgg cagctccttg ctcctaacag tggaggccag acttaggcac    1560
agcacaatgc ccaccaccac cagtgtgccg cacaaggccg tggcggtagg gtatgtgtct    1620
gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctagc tagatgcatg    1920
ctcgagcggc cgccagtgtg atggatatct gcagaattct atcttcagga tctcgccatg    1980
gagggtctta gcctactcca attgcccaga gataaatttc gaaaagctc tttctttgtt     2040 tgggtcatca tcttatttca aaaggccttt tccatgcctt tgggtgttgt gaccaacagc    2100
actttagaag taacagagat tgaccagcta gtctgcaagg atcatcttgc atcaactgac    2160
cagctgaaat cagttggtct caacctcgag gggagcggag tatctactga tatcccatct    2220
gcgacaaagc gttggggctt cagatctggt gtgcctcccc aagtggtcag ctatgaagca    2280
ggagaatggg ctgaaaattg ctacaatctt gaaataaaga aaccgacgg gagcgaatgc     2340 ttaccccac cgccggatgg tgtcagaggc tttccaaggt gccgctatgt tcacaaagcc     2400
caaggaaccg ggccctgccc gggtgactat gcctttcaca aggatggagc tttcttcctc    2460
tatgacaggc tggcttcaac tgtaatttac agaggagtca attttgctga ggggtaatc     2520 gcattcttga tattggctaa accaaaggaa acgttccttc aatcaccccc cattcgagag    2580
gcagcaaact acactgaaaa tacatcaagt tactatgcca catcctactt ggagtacgaa    2640
atcgaaaatt ttggtgctca acactccacg accctttca aaattaacaa taatactttt    2700
gttcttctgg acaggcccca cacgcctcag ttccttttcc agctgaatga taccattcaa    2760
cttcaccaac agttgagcaa cacaactggg aaactaattt ggacactaga tgctaatatc    2820
aatgctgata ttggtgaatg ggcttttttgg gaaaataaaa aaatctctcc gaacaactac    2880
gtggagaaga gctgtctttc gaaactttat cgctcaacga gacagaagac gatgatgcga    2940
catcgtcgag aactacaaag ggaagaatct ccgaccgggc caccaggaag tattcggacc    3000
tggttccaaa ggattcccct gggatggttt cattgcacgt accagaaggg gaaacaacat    3060
tgccgtctca gaattcgaca gaaggtcgaa gagtagatgt gaatactcag gaaactatca    3120
cagagacaac tgcaacaatc ataggcacta acggtaacaa catgcagatc tccaccatcg    3180
ggacaggact gagctccagc caaatcctga gttcctcacc gaccatggca ccaagccctg    3240
agactcagac ctccacaacc tacacaccaa aactaccagt gatgaccacc gaggaaccaa    3300
caacaccacc gagaaactct cctggctcaa caacagaagc acccactctc accacccag    3360 agaatataac aacagcggtt aaaactgttt gggcacaaga gtccacaagc aacggtctaa    3420
taacttcaac agtaacaggt attcttggga gccttggact tcgaaaacgc agcagaagac    3480
aagttaacac cagggccacg ggtaaatgca atcccaactt acactactgg actgcacaag    3540
aacaacataa tgctgctggg attgcctgga tcccgtactt tggaccgggt gcagaaggca    3600
tatacactga aggccttatg cacaaccaaa atgccttagt ctgtggactc agacaacttg    3660
caaatgaaac aactcaagct ctgcagcttt tcttaagggc cacgacgag ctgcggacat     3720 ataccatact caataggaag gccatagatt tccttctgcg acgatggggc gggacatgta    3780
ggatcctggg accagattgt tgcattgagc cacatgattg gaccaaaaac atcactgata    3840
aaatcaacca aatcatccat gatttcatcg acaacccttt acccaatcag gataatgatg    3900
```

```
ataattggtg acgggctgg agacagtgga tccctgcagg aataggcatt actggaatta    3960
ttattgcaat cattgctctt ctttgcgtct gcaagctgct tgttgaata tcagaattcc    4020
agcactggcg gccgttacta gtggatccga gctcggatcc aagctctaga ccaggcgcct   4080
ggatccagat ctgctgtgcc ttctagttgc cagccatctg ttgtttgccc ctccccgtg    4140
ccttccttga ccctgaaagg tgccactccc actgtccttt cctaataaaa tgaggaaatt   4200
gcatcgcatt gtctgagtag gtgtcattct attctggggg gtggggtggg gcagcacagc   4260
aaggggagg attgggaaga caatagcagg catgctgggg atgcggtggg ctctatgggt    4320
acccaggtgc tgaagaattg acccggttcc tcctgggcca gaaagaagca ggcacatccc   4380
cttctctgtg acacccctg tccacgcccc tggttcttag ttccagcccc actcatagga    4440
cactcatagc tcaggagggc tccgccttca atcccacccg ctaaagtact tggagcggtc   4500
tctccctccc tcatcagccc accaaaccaa acctagcctc caagagtggg aagaaattaa   4560
agcaagatag gctattaagt gcagagggag agaaaatgcc tccaacatgt gaggaagtaa   4620
tgagagaaat catagaattt cttccgcttc tcgctcact gactcgctgc gctcggtcgt    4680
tcggctgcgg cgagcggtat cagctcactc aaaggcggta atacggttat ccacagaatc   4740
aggggataac gcaggaaaga acatgtgagc aaaaggccag caaaaggcca ggaaccgtaa   4800
aaaggccgcg ttgctggcgt ttttccatag gctccgcccc cctgacgagc atcacaaaaa   4860
tcgacgctca agtcagaggt ggcgaaaccc gacaggacta taaagatacc aggcgtttcc   4920
ccctggaagc tccctcgtgc gctctcctgt tccgaccctg ccgcttaccg gatacctgtc   4980
cgcctttctc ccttcgggaa gcgtggcgct ttctcaatgc tcacgctgta ggtatctcag   5040
ttcggtgtag gtcgttcgct ccaagctggg ctgtgtgcac gaaccccccg ttcagcccga   5100
ccgctgcgcc ttatccggta actatcgtct tgagtccaac ccggtaagac acgacttatc   5160
gccactggca gcagccactg gtaacaggat tagcagagcg aggtatgtag gcggtgctac   5220
agagttcttg aagtggtggc ctaactacgg ctacactaga aggacagtat ttggtatctg   5280
cgctctgctg aagccagtta ccttcggaaa aagagttggt agctcttgat ccggcaaaca   5340
aaccaccgct ggtagcggtg gtttttttgt ttgcaagcag cagattacgc gcagaaaaaa   5400
aggatctcaa gaagatcctt tgatcttttc tacgggtctg acgctcagt ggaacgaaaa    5460
ctcacgttaa gggattttgg tcatgagatt atcaaaaagg atcttcacct agatcctttt   5520
aaattaaaaa tgaagtttta atcaatcta agtatatat gagtaaactt ggtctgacag      5580
ttaccaatgc ttaatcagtg aggcacctat ctcagcgatc tgtctatttc gttcatccat   5640
agttgcctga ctccgggggg gggggcgct gaggtctgcc tcgtgaagaa ggtgttgctg     5700
actcatacca ggcctgaatc gccccatcat ccagccagaa agtgagggag ccacggttga   5760
tgagagcttt gttgtaggtg gaccagttgg tgattttgaa cttttgcttt gccacggaac   5820
ggtctgcgtt gtcgggaaga tgcgtgatct gatccttcaa ctcagcaaaa gttcgattta   5880
ttcaacaaag ccgccgtccc gtcaagtcag cgtaatgctc tgccagtgtt acaaccaatt   5940
aaccaattct gattagaaaa actcatcgag catcaaatga aactgcaatt tattcatatc   6000
aggattatca ataccatatt tttgaaaaag ccgtttctgt aatgaaggag aaaactcacc   6060
gaggcagttc cataggatgg caagatcctg gtatcggtct gcgattccga ctcgtccaac   6120
atcaatacaa cctattaatt tcccctcgtc aaaaataagg ttatcaagtg agaaatcacc   6180
atgagtgacg actgaatccg gtgagaatgg caaaagctta tgcatttctt tccagacttg   6240
```

-continued

```
ttcaacaggc cagccattac gctcgtcatc aaaatcactc gcatcaacca aaccgttatt      6300
cattcgtgat tgcgcctgag cgagacgaaa tacgcgatcg ctgttaaaag gacaattaca      6360
aacaggaatc gaatgcaacc ggcgcaggaa cactgccagc gcatcaacaa tattttcacc      6420
tgaatcagga tattcttcta atacctggaa tgctgttttc ccggggatcg cagtggtgag      6480
taaccatgca tcatcaggag tacgataaaa tgcttgatg gtcggaagag cataaaattc       6540
cgtcagccag tttagtctga ccatctcatc tgtaacatca ttggcaacgc tacctttgcc      6600
atgtttcaga acaactctg gcgcatcggg cttcccatac aatcgataga ttgtcgcacc       6660
tgattgcccg acattatcgc gagcccattt atacccatat aaatcagcat ccatgttgga     6720
atttaatcgc ggcctcgagc aagacgtttc ccgttgaata tggctcataa cacccccttgt    6780 attactgttt atgtaagcag acagtttttat tgttcatgat gatatatttt tatcttgtgc    6840
aatgtaacat cagagatttt gagacacaac gtggctttcc ccccccccc attattgaag      6900 catttatcag ggttattgtc tcatgagcgg atacatattt gaatgtattt agaaaaataa     6960
acaaataggg gttccgcgca catttccccg aaaagtgcca cctgacgtct aagaaaccat     7020
tattatcatg acattaacct ataaaaatag gcgtatcacg aggccctttc gtc             7073
```

<210> SEQ ID NO 3
<211> LENGTH: 7285
<212> TYPE: DNA
<213> ORGANISM: Artificial Sequence
<220> FEATURE:
<223> OTHER INFORMATION: Description of Artificial Sequence:Plasmid
containing DNA of GP of Ebola Virus, Zaire strain
<221> NAME/KEY: 5'UTR
<222> LOCATION: (886)..(1129)
<223> OTHER INFORMATION: CMV IE 5' UT
<221> NAME/KEY: intron
<222> LOCATION: (1130)..(1840)
<223> OTHER INFORMATION: CMV IE INT
<221> NAME/KEY: enhancer
<222> LOCATION: (248)..(885)
<223> OTHER INFORMATION: CMV enhancer
<221> NAME/KEY: gene
<222> LOCATION: (1870)..(4301)
<223> OTHER INFORMATION: GP(Z)
<221> NAME/KEY: gene
<222> LOCATION: (4302)..(4854)
<223> OTHER INFORMATION: TbGH
<221> NAME/KEY: gene
<222> LOCATION: (6350)..(6972)
<223> OTHER INFORMATION: Kan r

<400> SEQUENCE: 3

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg      120 ttggcgggtg tcgggctgg cttaactatg cggcatcaga gcagattgta ctgagagtgc      180
accatatgcg gtgtgaaata ccgcacagat gcgtaaggag aaaataccgc atcagattgg      240
ctattggcca ttgcatacgt tgtatccata tcataatatg tacatttata ttggctcatg      300
tccaacatta ccgccatgtt gacattgatt attgactagt tattaatagt aatcaattac     360
ggggtcatta gttcatagcc catatatgga gttccgcgtt acataactta cggtaaatgg      420
cccgcctggc tgaccgccca acgacccccg cccattgacg tcaataatga cgtatgttcc      480
catagtaacg ccaataggga ctttccattg acgtcaatgg gtggagtatt tacggtaaac      540
tgcccacttg gcagtacatc aagtgtatca tatgccaagt acgccccta ttgacgtcaa       600 tgacggtaaa tggcccgcct ggcattatgc ccagtacatg accttatggg actttcctac      660
```

-continued

```
ttggcagtac atctacgtat tagtcatcgc tattaccatg gtgatgcggt tttggcagta      720
catcaatggg cgtggatagc ggttttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag    900
agctcgttta gtgaaccgtc agatcgcctg gagacgccat ccacgctgtt ttgacctcca    960
tagaagacac cgggaccgat ccagcctccg cggccgggaa cggtgcattg gaacgcggat    1020
tccccgtgcc aagagtgacg taagtaccgc ctatagactc tataggcaca ccccttttggc   1080 tcttatgcat gctatactgt ttttggcttg gggcctatac ccccgcttc ccttatgcta    1140 taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tattttaca    1320 ggatggggtc ccatttatta tttacaaatt cacatataca acaacgccgt ccccgtgcc    1380 cgcagttttt attaaacata gcgtgggatc tccacgcgaa tctcgggtac gtgttccgga   1440
catgggctct tctccggtag cggcggagct tccacatccg agccctggtc ccatgcctcc   1500
agcggctcat ggtcgctcgg cagctccttg ctcctaacag tggaggccag acttaggcac    1560
agcacaatgc ccaccaccac cagtgtgccg cacaaggccg tggcggtagg gtatgtgtct   1620
gaaaatgagc gtggagattg ggctcgcacg gctgacgcag atggaagact taaggcagcg   1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg   1800
cgcgccacca gacataatag ctgacagact aacagactgt tcctttccat gggtcttttc    1860
tgcagtcacc gtcgtcgaca cgtgtgatca gatatcgcgg ccgctctaga ccaggcgcct    1920
ggatcgatcc gcgatgaaga ttaagccgac agtgagcgta atcttcatct ctcttagatt    1980
atttgttttc cagagtaggg gtcgtcaggt ccttttcaat cgtgtaacca aaataaactc    2040
cactagaagg atattgtggg gcaacaacac aatgggcgtt acaggaatat tgcagttacc    2100
tcgtgatcga ttcaagagga catcattctt tctttgggta attatccttt tccaaagaac    2160
attttccatc ccacttggag tcatccacaa tagcacatta caggttagtg atgtcgacaa    2220
actagtttgt cgtgacaaac tgtcatccac aaatcaattg agatcagttg gactgaatct    2280
cgaagggaat ggagtggcaa ctgacgtgcc atctgcaact aaaagatggg gcttcaggtc    2340
cggtgtccca ccaaaggtgg tcaattatga agctggtgaa tgggctgaaa actgctacaa    2400
tcttgaaatc aaaaaacctg acgggagtga gtgtctacca gcagcgccag acgggattcg    2460
gggcttcccc cggtgccggt atgtgcacaa agtatcagga acgggaccgt gtgccggaga    2520
ctttgccttc cataaagagg gtgctttctt cctgtatgat cgacttgctt ccacagttat    2580
ctaccgagga acgactttcg ctgaaggtgt cgttgcattt ctgatactgc cccaagctaa    2640
gaaggacttc ttcagctcac accccttgag agagccggtc aatgcaacgg aggacccgtc    2700
tagtggctac tattctacca caattagata tcaggctacc ggttttggaa ccaatgagac    2760
agagtacttg ttcgaggttg acaatttgac ctacgtccaa cttgaatcaa gattcacacc    2820
acagtttctg ctccagctga atgagacaat atatacaagt gggaaagga gcaataccac    2880 gggaaaacta atttggaagg tcaaccccga aattgataca acaatcgggg agtgggcctt    2940
ctgggaaact aaaaaaaacc tcactagaaa aattcgcagt gaagagttgt cctttcacagt    3000 tgtatcaaac ggagccaaaa acatcagtgg tcagagtccg gcgcgaactt cttccgaccc    3060
```

```
agggaccaac acaacaactg aagaccacaa aatcatggct tcagaaaatt cctctgcaat    3120
ggttcaagtg cacagtcaag gaagggaagc tgcagtgtcg catctaacaa cccttgccac    3180
aatctccacg agtccccaat ccctcacaac caaaccaggt ccggacaaca gcacccataa    3240
tacacccgtg tataaacttg acatctctga ggcaactcaa gttgaacaac atcaccgcag    3300
aacagacaac gacagcacag cctccgacac tccctctgcc acgaccgcag ccggaccccc    3360
aaaagcagag aacaccaaca cgagcaagag cactgacttc ctggaccccg ccaccacaac    3420
aagtccccaa aaccacagcg agaccgctgg caacaacaac actcatcacc aagataccgg    3480
agaagagagt gccagcagcg ggaagctagg cttaattacc aatactattg ctggagtcgc    3540
aggactgatc acaggcggga gaagaactcg aagagaagca attgtcaatg ctcaacccaa    3600
atgcaaccct aatttacatt actggactac tcaggatgaa ggtgctgcaa tcggactggc    3660
ctggatacca tatttcgggc cagcagccga gggaatttac atagaggggc taatgcacaa    3720
tcaagatggt ttaatctgtg ggttgagaca gctggccaac gagacgactc aagctcttca    3780
actgttcctg agagccacaa ctgagctacg caccttttca atcctcaacc gtaaggcaat    3840
tgatttcttg ctgcagcgat ggggcggcac atgccacatt ctgggaccgg actgctgtat    3900
cgaaccacat gattggacca agaacataac agacaaaatt gatcagatta ttcatgattt    3960
tgttgataaa ccccttccgg accaggggga caatgacaat tggtggacag gatggagaca    4020
atggataccg gcaggtattg gagttacagg cgttataatt gcagttatcg ctttattctg    4080
tatatgcaaa tttgtctttt agttttttct tcagattgct tcatggaaaag ctcagcctca    4140 aatcaatgaa accaggattt aattatatgg attacttgaa tctaagatta cttgacaaat    4200
gataatataa tacactggag ctttaaacat agccaatgtg attctaactc ctttaaactc    4260
acagttaatc ataaacaagg tttggtaccg agctcgaatt atctgctgtg ccttctagtt    4320
gccagccatc tgttgtttgc ccctcccccg tgccttcctt gaccctggaa ggtgccactc    4380
ccactgtcct ttcctaataa aatgaggaaa ttgcatcgca ttgtctgagt aggtgtcatt    4440
ctattctggg gggtggggtg gggcagcaca gcaaggggga ggattgggaa gacaatagca    4500
ggcatgctgg ggatgcggtg ggctctatgg gtacccaggt gctgaagaat tgacccggtt    4560
cctcctgggc cagaaagaag caggcacatc cccttctctg tgacacaccc tgtccacgcc    4620
cctggttctt agttccagcc ccactcatag gacactcata gctcaggagg ctccgccttt    4680
caatcccacc cgctaaagta cttggagcgg tctctccctc cctcatcagc ccaccaaacc    4740
aaacctagcc tccaagagtg ggaagaaatt aaagcaagat aggctattaa gtgcagaggg    4800
agagaaaatg cctccaacat gtgaggaagt aatgagagaa atcatagaat tcttccgct     4860 tcctcgctca ctgactcgct gcgctcggtc gttcggctgc ggcgagcggt atcagctcac    4920
tcaaaggcgg taatacggtt atccacagaa tcagggggata acgcaggaaa gaacatgtga    4980
gcaaaaggcc agcaaaaggc caggaaccgt aaaaaggccg cgttgctggc gtttttccat    5040
aggctccgcc cccctgacga gcatcacaaa aatcgacgct caagtcagag gtggcgaaac    5100
ccgacaggac tataaagata ccaggcgttt ccccctggaa gctccctcgt gcgctctcct    5160
gttccgaccc tgccgcttac cggatacctg tccgcctttc tcccttcggg aagcgtggcg    5220
ctttctcaat gctcacgctg taggtatctc agttcggtgt aggtcgttcg ctccaagctg    5280
ggctgtgtgc acgaaccccc cgttcagccc gaccgctgcg ccttatccgg taactatcgt    5340
cttgagtcca acccggtaag acacgactta tcgccactgg cagcagccac tggtaacagg    5400
```

```
attagcagag cgaggtatgt aggcggtgct acagagttct tgaagtggtg gcctaactac    5460
ggctacacta gaaggacagt atttggtatc tgcgctctgc tgaagccagt taccttcgga    5520
aaaagagttg gtagctcttg atccggcaaa caaaccaccg ctggtagcgg tggtttttttt   5580 gtttgcaagc agcagattac gcgcagaaaa aaaggatctc aagaagatcc tttgatcttt    5640
tctacggggt ctgacgctca gtggaacgaa aactcacgtt aagggatttt ggtcatgaga    5700
ttatcaaaaa ggatcttcac ctagatcctt ttaaattaaa aatgaagttt taaatcaatc    5760
taaagtatat atgagtaaac ttggtctgac agttaccaat gcttaatcag tgaggcacct    5820
atctcagcga tctgtctatt tcgttcatcc atagttgcct gactccgggg ggggggggcg    5880
ctgaggtctg cctcgtgaag aaggtgttgc tgactcatac caggcctgaa tcgccccatc    5940
atccagccag aaagtgaggg agccacggtt gatgagagct tgttgtagg tggaccagtt     6000 ggtgattttg aacttttgct tgccacggaa acggtctgcg ttgtcgggaa gatgcgtgat    6060
ctgatccttc aactcagcaa aagttcgatt tattcaacaa agccgccgtc ccgtcaagtc    6120
agcgtaatgc tctgccagtg ttacaaccaa ttaaccaatt ctgattagaa aaactcatcg    6180
agcatcaaat gaaactgcaa tttattcata tcaggattat caataccata tttttgaaaa    6240
agccgtttct gtaatgaagg agaaaactca ccgaggcagt tccataggat ggcaagatcc    6300
tggtatcggt ctgcgattcc gactcgtcca acatcaatac aacctattaa tttcccctcg    6360 tcaaaataa ggttatcaag tgagaaatca ccatgagtga cgactgaatc cggtgagaat     6420
ggcaaaagct tatgcatttc tttccagact tgttcaacag gccagccatt acgctcgtca    6480
tcaaaatcac tcgcatcaac caaaccgtta ttcattcgtg attgcgcctg agcgagacga    6540
aatacgcgat cgctgttaaa aggacaatta caaacaggaa tcgaatgcaa ccggcgcagg    6600
aacactgcca gcgcatcaac aatattttca cctgaatcag gatattcttc taatacctgg    6660
aatgctgttt tcccggggat cgcagtggtg agtaaccatg catcatcagg agtacggata    6720
aaatgcttga tggtcggaag aggcataaat tccgtcagcc agtttagtct gaccatctca    6780
tctgtaacat cattggcaac gctacctttg ccatgtttca gaaacaactc tggcgcatcg    6840
ggcttcccat acaatcgata gattgtcgca cctgattgcc cgacattatc gcgagcccat    6900
ttatacccat ataaatcagc atccatgttg gaatttaatc gcggcctcga gcaagacgtt    6960
tcccgttgaa tatggctcat aacaccccett gtattactgt ttatgtaagc agacagtttt    7020
attgttcatg atgatatatt tttatcttgt gcaatgtaac atcagagatt ttgagacaca    7080
acgtggcttt cccccccccc ccattattga agcatttatc agggttattg tctcatgagc    7140
ggatacatat ttgaatgtat ttagaaaaat aaacaaatag gggttccgcg cacatttccc    7200
cgaaaagtgc cacctgacgt ctaagaaacc attattatca tgacattaac ctataaaaat    7260
aggcgtatca cgaggccctt tcgtc                                          7285
```

<210> SEQ ID NO 4
<211> LENGTH: 7272
<212> TYPE: DNA
<213> ORGANISM: Artificial Sequence
<220> FEATURE:
<223> OTHER INFORMATION: Description of Artificial Sequence:Plasmid
      containing DNA for soluble GP of Ebola Virus,
      Zaire strain
<221> NAME/KEY: 5'UTR
<222> LOCATION: (886)..(1129)
<223> OTHER INFORMATION: CMV IE 5' UT
<221> NAME/KEY: intron
<222> LOCATION: (1130)..(1840)
<223> OTHER INFORMATION: CMV IE INT

```
<221> NAME/KEY: enhancer
<222> LOCATION: (248)..(885)
<223> OTHER INFORMATION: CMV enhancer
<221> NAME/KEY: gene
<222> LOCATION: (1870)..(4288)
<223> OTHER INFORMATION: SGP(Z)
<221> NAME/KEY: gene
<222> LOCATION: (4289)..(4841)
<223> OTHER INFORMATION: TbGH
<221> NAME/KEY: gene
<222> LOCATION: (6337)..(6959)
<223> OTHER INFORMATION: Kan r

<400> SEQUENCE: 4
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctggc ttaactatgc ggcatcagag cagattgtac tgagagtgc      180 accatatgcg gtgtgaaata ccgcacagat gcgtaaggag aaaataccgc atcagattgg     240
ctattggcca ttgcatacgt tgtatccata tcataatatg tacatttata ttggctcatg     300
tccaacatta ccgccatgtt gacattgatt attgactagt tattaatagt aatcaattac     360
ggggtcatta gttcatagcc catatatgga gttccgcgtt acataactta cggtaaatgg     420
cccgcctggc tgaccgccca acgacccccg cccattgacg tcaataatga cgtatgttcc     480
catagtaacg ccaataggga ctttccattg acgtcaatgg gtggagtatt tacggtaaac     540
tgcccacttg gcagtacatc aagtgtatca tatgccaagt acgccccta ttgacgtcaa      600 tgacggtaaa tggcccgcct ggcattatgc ccagtacatg accttatggg actttcctac     660
ttggcagtac atctacgtat tagtcatcgc tattaccatg gtgatgcggt tttggcagta     720
catcaatggg cgtggatagc ggtttgactc acggggattt ccaagtctcc accccattga     780
cgtcaatggg agtttgtttt ggcaccaaaa tcaacgggac tttccaaaat gtcgtaacaa     840
ctccgcccca ttgacgcaaa tgggcggtag gcgtgtacgg tgggaggtct atataagcag     900
agctcgttta gtgaaccgtc agatcgcctg gagacgccat ccacgctgtt ttgacctcca     960
tagaagacac cgggaccgat ccagcctccg gggccgggaa cggtgcattg gaacgcggat    1020
tccccgtgcc aagagtgacg taagtaccgc ctatagactc tataggcaca cccctttggc    1080
tcttatgcat gctatactgt ttttggcttg gggcctatac accccgcgtt ccttatgcta    1140
taggtgatgg tatagcttag cctataggtg tgggttattg accattattg accactcccc    1200
tattggtgac gatactttcc attactaatc cataacatgg ctctttgcca caactatctc    1260
tattggctat atgccaatac tctgtccttc agagactgac acggactctg tatttttaca    1320
ggatggggtc ccattattat tttacaaatt cacatataca caacgccgt ccccgtgcc      1380 cgcagttttt attaaacata gcgtgggatc tccacgcgaa tctcgggtac gtgttccgga    1440
catggctctc tccggtagcg gcggagct tccacatccg agccctggtc catgcctcc       1500 agcggctcat ggtcgctcgg cagctccttg ctcctaacag tggaggccag acttaggcac    1560
agcacaatgc ccaccaccac cagtgtgccg cacaaggccg tggcgtagg gtatgtgtct     1620 gaaaatgagc gtggagattg ggctcgcacg gctgacgcag atggaagact taaggcagcg    1680
gcagaagaag atgcaggcag ctgagttgtt gtattctgat aagagtcaga ggtaactccc    1740
gttgcggtgc tgttaacggt ggagggcagt gtagtctgag cagtactcgt tgctgccgcg    1800
cgcgccacca gacataatag ctgacagact aacagactgt tcctttccat gggtcttttc    1860
tgcagtcacc gtcgtcgaca cgtgtgatca gatatcgcgg ccgctctaga ccaggcgcct    1920
```

```
ggatcgaatt gatgaagatt aagccgacag tgagcgtaat cttcatctct cttagattat    1980
ttgttttcca gagtaggggt cgtcaggtcc ttttcaatcg tgtaaccaaa ataaactcca    2040
ctagaaggat attgtgggc aacaacacaa tgggcgttac aggaatattg cagttacctc    2100
gtgatcgatt caagaggaca tcattctttc tttgggtaat tatccttttc caaagaacat    2160
tttccatccc acttggagtc atccacaata gcacattaca ggttagtgat gtcgacaaac    2220
tagtttgtcg tgacaaactg tcatccacaa atcaattgag atcagttgga ctgaatctcg    2280
aagggaatgg agtggcaact gacgtgccat ctgcaactaa agatggggc ttcaggtccg     2340
gtgtcccacc aaaggtggtc aattatgaag ctggtgaatg ggctgaaaac tgctacaatc    2400
ttgaaatcaa aaaacctgac gggagtgagt gtctaccagc agcgccagac gggattcggg    2460
gcttcccccg gtgccggtat gtgcacaaag tatcaggaac gggaccgtgt gccgagact    2520
ttgccttcca taaagagggt gctttcttcc tgtatgatcg acttgcttcc acagttatct    2580
accgaggaac gactttcgct gaaggtgtcg ttgcatttct gatactgccc caagctaaga    2640
aggacttctt cagctcacac cccttgagag agccggtcaa tgcaacggag acccgtcta    2700
gtggctacta ttctaccaca attagatatc aggctaccgg ttttggaacc aatgagacag    2760
agtacttgtt cgaggttgac aatttgacct acgtccaact tgaatcaaga ttcacaccac    2820
agtttctgct ccagctgaat gagacaatat atacaagtgg gaaaggagc aataccacgg     2880
gaaaactaat ttggaaggtc aaccccgaaa ttgatacaac aatcggggag tgggccttct    2940
gggaaactaa aaaaacctca ctagaaaaat tcgcagtgaa gagttgtctt tcacagttgt    3000
atcaaacgga gccaaaaaca tcagtggtca gagtccggcg cgaacttctt ccgacccagg    3060
gaccaacaca caactgaag accacaaaat catggcttca gaaaattcct ctgcaatggt      3120
tcaagtgcac agtcaaggaa gggaagctgc agtgtcgcat ctaacaaccc ttgccacaat    3180
ctccacgagt ccccaatccc tcacaaccaa accaggtccg gacaacagca cccataatac    3240
acccgtgtat aaacttgaca tctctgaggc aactcaagtt gaacaacatc accgcagaac    3300
agacaacgac agcacagcct ccgacactcc ctctgccacg accgcagccg gaccccaaa     3360
agcagagaac accaacacga gcaagagcac tgacttcctg gaccccgcca ccacaacaag    3420
tccccaaaac cacagcgaga ccgctggcaa caacaacact catcaccaag ataccggaga    3480
agagagtgcc agcagcggga agctaggctt aattaccaat actattgctg gagtcgcagg    3540
actgatcaca gcggagaa gaactcgaag agaagcaatt gtcatgctc aacccaaatg       3600
caaccctaat ttacattact ggactactca ggatgaaggt gctgcaatcg gactggcctg    3660
gataccatat ttcgggccag cagccgaggg aatttacata gagggctaa tgcacaatca    3720
agatggttta atctgtgggt tgagacagct ggccaacgag acgactcaag ctcttcaact    3780
gttcctgaga gccacaactg agctacgcac cttttcaatc ctcaaccgta aggcaattga    3840
tttcttgctg cagcgatggg gcggcacatg ccacattctg ggaccggact gctgtatcga    3900
accacatgat tggaccaaga acataacaga caaaattgat cagattattc atgattttgt    3960
tgataaaacc cttccggacc aggggacaa tgacaattgg tggacaggat ggagacaatg     4020
gataccggca ggtattggag ttacaggcgt tataattgca gttatcgctt tattctgtat    4080
atgcaaattt gtctttttagt ttttcttcag attgcttcat ggaaaagctc agcctcaaat    4140
caatgaaacc aggatttaat tatatggatt acttgaatct aagattactt gacaaatgat    4200
aatataatac actggagctt taaacatagc caatgtgatt ctaactcctt taaactcaca    4260
gttaatcata aacaaggttt ggaattgatc tgctgtgcct tctagttgcc agccatctgt    4320
```

```
tgtttgcccc tccccgtgc cttccttgac cctggaaggt gccactccca ctgtcctttc    4380
ctaataaaat gaggaaattg catcgcattg tctgagtagg tgtcattcta ttctgggggg    4440
tggggtgggg cagcacagca aggggagga ttgggaagac aatagcaggc atgctgggga    4500
tgcggtgggc tctatgggta cccaggtgct gaagaattga cccggttcct cctgggccag    4560
aaagaagcag gcacatcccc ttctctgtga cacaccctgt ccacgcccct ggttcttagt    4620
tccagcccca ctcataggac actcatagct caggagggct ccgccttcaa tcccacccgc    4680
taaagtactt ggagcggtct ctccctccct catcagccca ccaaaccaaa cctagcctcc    4740
aagagtggga agaaattaaa gcaagatagg ctattaagtg cagagggaga gaaaatgcct    4800
ccaacatgtg aggaagtaat gagagaaatc atagaatttc ttccgcttcc tcgctcactg    4860
actcgctgcg ctcggtcgtt cggctgcggc gagcggtatc agctcactca aaggcggtaa    4920
tacggttatc cacagaatca ggggataaca caggaaagaa catgtgagca aaaggccagc    4980
aaaaggccag gaaccgtaaa aaggccgcgt tgctggcgtt tttccatagg ctccgccccc    5040
ctgacgagca tcacaaaaat cgacgctcaa gtcagaggtg gcgaaacccg acaggactat    5100
aaagatacca ggcgtttccc cctggaagct ccctcgtgcg ctctcctgtt ccgaccctgc    5160
cgcttaccgg atacctgtcc gcctttctcc cttcgggaag cgtggcgctt tctcaatgct    5220
cacgctgtag gtatctcagt tcggtgtagg tcgttcgctc caagctgggc tgtgtgcacg    5280
aacccccccgt tcagcccgac cgctgcgcct tatccggtaa ctatcgtctt gagtccaacc    5340
cggtaagaca cgacttatcg ccactggcag cagccactgg taacaggatt agcagagcga    5400
ggtatgtagg cggtgctaca gagttcttga agtggtggcc taactacggc tacactagaa    5460
ggacagtatt tggtatctgc gctctgctga agccagttac cttcggaaaa agagttggta    5520
gctcttgatc cggcaaacaa accaccgctg gtagcggtgg tttttttgtt gcaagcagc    5580
agattacgcg cagaaaaaaa ggatctcaag aagatccttt gatcttttct acggggtctg    5640
acgctcagtg gaacgaaaac tcacgttaag ggattttggt catgagatta tcaaaaagga    5700
tcttcaccta gatcctttta aattaaaaat gaagttttaa atcaatctaa agtatatatg    5760
agtaaacttg gtctgacagt taccaatgct taatcagtga ggcacctatc tcagcgatct    5820
gtctatttcg ttcatccata gttgcctgac tccggggggg ggggcgctg aggtctgcct    5880
cgtgaagaag gtgttgctga ctcataccag gcctgaatcg ccccatcatc cagccagaaa    5940
gtgagggagc cacggttgat gagagctttg ttgtaggtgg accagttggt gattttgaac    6000
ttttgctttg ccacggaacg gtctgcgttg tcgggaagat gcgtgatctg atccttcaac    6060
tcagcaaaag ttcgatttat tcaacaaagc cgccgtcccg tcaagtcagc gtaatgctct    6120
gccagtgtta caaccaatta accaattctg attagaaaaa ctcatcgagc atcaaatgaa    6180
actgcaattt attcatatca ggattatcaa taccatattt tgaaaaagc cgtttctgta    6240
atgaaggaga aaactcaccg aggcagttcc ataggatggc aagatcctgg tatcggtctg    6300
cgattccgac tcgtccaaca tcaatacaac ctattaattt cccctcgtca aaataaggt    6360
tatcaagtga gaaatcacca tgagtgacga ctgaatccgg tgagaatggc aaaagcttat    6420
gcatttcttt ccagacttgt tcaacaggcc agccattacg ctcgtcatca aaatcactcg    6480
catcaaccaa accgttattc attcgtgatt gcgcctgagc gagacgaaat acgcgatcgc    6540
tgttaaaagg acaattacaa acaggaatcg aatgcaaccg gcgcaggaac actgccagcg    6600
catcaacaat attttcacct gaatcaggat attcttctaa tacctggaat gctgttttcc    6660
```

```
-continued cggggatcgc agtggtgagt aaccatgcat catcaggagt acggataaaa tgcttgatgg    6720
tcggaagagg cataaattcc gtcagccagt ttagtctgac catctcatct gtaacatcat    6780
tggcaacgct acctttgcca tgtttcagaa acaactctgg cgcatcgggc ttcccataca    6840
atcgatagat tgtcgcacct gattgcccga cattatcgcg agcccattta tacccatata    6900
aatcagcatc catgttggaa tttaatcgcg gcctcgagca agacgtttcc cgttgaatat    6960
ggctcataac acccttgta ttactgttta tgtaagcaga cagttttatt gttcatgatg     7020
atatattttt atcttgtgca atgtaacatc agagattttg agacacaacg tggctttccc    7080 cccccccca ttattgaagc atttatcagg gttattgtct catgagcgga tacatatttg     7140
aatgtattta gaaaaataaa caaatagggg ttccgcgcac atttccccga aaagtgccac    7200
ctgacgtcta agaaaccatt attatcatga cattaaccta taaaaatagg cgtatcacga    7260
ggccctttcg tc                                                       7272
```

US 6,852,324 B1

IMMUNIZATION FOR EBOLA VIRUS INFECTION

RELATED APPLICATIONS

This application is the National Stage of International Application No. PCT/US98/27364, filed 23 Dec. 1998, designating the United States of America and published in English on 1 Jul. 1999 as WO 99/32147, which claims the benefit of priority of U.S. Provisional Application No. 90/068,655 filed 23 Dec. 1997.

FIELD OF THE INVENTION

The present invention relates generally to viral vaccines and, more particularly, to Ebola virus vaccines and methods of protecting against disease caused by infection with Ebola virus.

BACKGROUND OF THE INVENTION

The Ebola viruses, and the genetically-related Marburg virus, are filoviruses associated with outbreaks of highly lethal hemorrhagic fever in humans and primates in North America, Europe, and Africa. Peters, C. J. et al., *Filoviridae*: Marburg and Ebola Viruses. in *Fields Virology*. (eds., Fields, B. N., Knipe, D. M.& Howley, P. M.) 1161–1176 (Philadelphia, Lippincott-Raven, 1996); Peters, C. J. et al, *Semin. Virol* 5:147–154 (1994). Ebola viruses are negative-stranded RNA viruses comprised of four subtypes, including those described in the Zaire, Sudan, Reston, and Ivory Coast episodes. Sanchez, A. et al., *PNAS (USA)* 93:3602–3607 (1996). Although several subtypes have been defined, the genetic organization of these viruses is similar, each containing seven linearly arrayed genes. Among the viral proteins, the envelope glycoprotein exists in two alternative forms, a 50–70 kilodalton (kDa) secreted protein of unknown function encoded by the viral genome and a 130 kDa transmembrane glycoprotein generated by RNA editing that mediates viral entry. Peters, C. J. et al., *Filoviridae*: Marburg and Ebola Viruses. in *Fields Virology*. (eds., Fields, B. N., Knipe, D. M.& Howley, P. M.) 1161–1176 (Philadelphia, Lippincott-Raven, 1996); Sanchez, A. et al., *PNAS (USA)* 93:3602–3607 (1996). Other structural gene products include the nucleoprotein (NP), matrix proteins VP24 and VP40, presumed nonstructural proteins VP30 and VP35, and the viral polymerase (reviewed in Peters, C. J. et al., *Filoviridae*: Marburg and Ebola Viruses. in *Fields Virology*. (eds., Fields, B. N., Knipe, D. M.& Howley, P. M.) 1161–1176 (Philadelphia, Lippincott-Raven, 1996)). Although spontaneous variation of its RNA sequence does occur in nature, there appears to be less nucleotide polymorphism within Ebola subtypes than among other RNA viruses (Sanchez, A. et al., *PNAS (USA)* 93:3602–3607 (1996)), suggesting that immunization may be useful in protecting against this disease. Previous attempts to elicit protective immune responses against Ebola virus using traditional active and passive immunization approaches have, however, not succeeded. Peters, C. J. et al., *Filoviridae*: Marburg and Ebola Viruses. in *Fields Virology*. (eds., Fields, B. N., Knipe, D. M.& Howley, P. M.) 1161–1176 (Philadelphia, Lippincott-Raven, 1996); Clegg, J. C. S. et al., *New Generation Vaccines*. (eds., Levine, M. M., Woodrow, G. C., Kaper, J. B.& Cobon, G. S.) 749–765 (New York, N.Y., Marcel Dekker, Inc. 1997); Jahrling, P. B. et al., *Arch. Virol. Suppl.* 11:135–140 (1996).

It would thus be desirable to provide a vaccine to protect against disease caused by infection with Ebola virus. It would further be desirable to provide methods of making and using said vaccine.

SUMMARY OF THE INVENTION

Ebola virus vaccines comprising nucleic acid molecules encoding Ebola viral proteins are provided. In one embodiment, the nucleic acid molecule encodes the transmembrane form of the viral glycoprotein (GP). In another embodiment, the nucleic acid molecule encodes the secreted form of the viral glycoprotein (sGP). In yet another embodiment, the nucleic acid molecule encodes the viral nucleoprotein (NP).

The present invention also provides methods for immunizing a subject against disease caused by infection with Ebola virus comprising administering to the subject an immunoeffective amount of an Ebola virus vaccine. Administration can be by any of the routes normally used for gene therapy. In a preferred method, the Ebola virus vaccine is administered by intramuscular injection. The genetic immunization methods of the present invention provide protective immunity against disease caused by infection with Ebola virus.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings.

FIGS. 1A and 1B are photographs showing expression of Ebola virus gene products in eukaryotic plasmid expression vectors.

FIG. 1A. Expression vectors encoding the indicated viral gene products under regulation of the CMV immediate-early region 1 enhancer and promoter were prepared and transfected into 293 cells as previously described. Manthorpe, M. et al. *Hum. Gene. Ther.* 4:419–431 (1993); Sambrook, J., Fritch, E. F., & Maniatis, T. Cold Spring Harbor, N.Y. Cold Spring Laboratory Harbor Press, 1994. Cell extracts were prepared and analyzed by Western blot analysis for NP (left) or GP (right) using relevant rabbit antisera and a secondary antibody, horseradish peroxidase conjugated donkey anti-rabbit IgG of a dilution of 1:5,000. Incubation with primary antibody was for 30 minutes at room temperature, and for 30 minutes at room temperature with secondary antibody. Immunocomplexes were then detected by chemiluminescence using super signal substrate reagents (Pierce) according to manufacturer's instructions.

FIG. 1B. Generation of antibody response in mice immunized with the indicated vectors and analyzed by Western blot for NP, GP, and sGP as shown.

Antisera from mice were tested at a dilution of 1:500 (NP), 1:50 (GP), or 1:50 (sGP), respectively, and developed with a secondary antibody (sheep anti-mouse, 1:5,000, Amersham Life Science) and chemiluminescence as in FIG. 1A. The control vector used for immunization represents the expression vector plasmid with no insert. Manthorpe, M. et al., *Hum. Gene. Ther.* 4:419431 (1993).

FIGS. 2A–2D are graphs showing the immune responses to NP and GP after genetic immunization in mice.

Figure 2A:
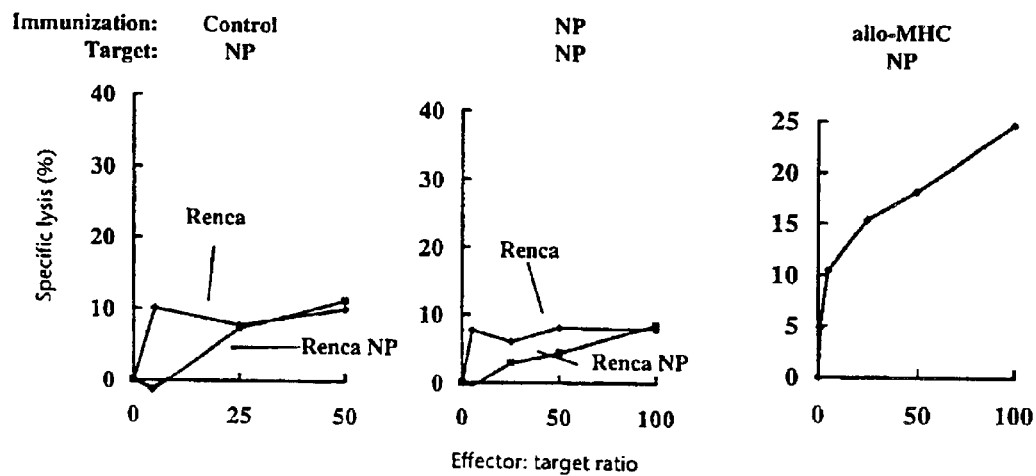

FIG. 2A. Splenic lymphocytes from vector or NP-plasmid immunized mice were isolated approximately 6 weeks after the initial immunization and sensitized in vitro for 5 days with 10 U/ml hIL-2. Renca-NP cells sensitized splenocytes from vector-immunized or pCMV-NP immunized mice were used to detect CTL activity at the indicated effector:target ratios on Renca or Renca-NP cells (left, middle) or with allogeneic effector cells with Renca-NP to show that they are susceptible to lysis (right). Allogeneic effector cells were generated by incubating cells derived from mice with a C57BI/6 background ($5\times10^6$/ml) with irradiated Balb/c spleen cells ($5\times10^6$/ml) in the presence of IL-2 (20 U/ml) for five days. The chromium release CTL assay with Renca-NP cells was performed in triplicate as previously described. Ohno, T. et al., *Gene. Ther.* 4:361–366 (1997).

Figure 2B:
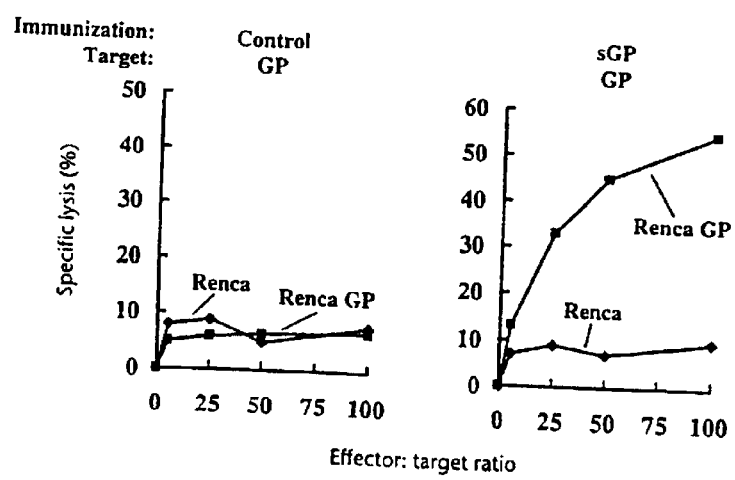

FIG. 2B. Balb/C female mice were immunized with the sGP plasmid expression vector and analyzed for their ability to lyse the syngeneic Renca cell line stably expressing GP. Isolation of stable transfectants, confirmation of expression, and CTL assay were performed as described (see, Specific Example, II. Methods). Renca-GP or sGP sensitized splenocytes from pCMV-GP or pCMV-sGP immunized mice were used to determine the specific killing of $^{51}$chromium labeled Renca-GP cells at the indicated E/T ratios.

Figure 2C:
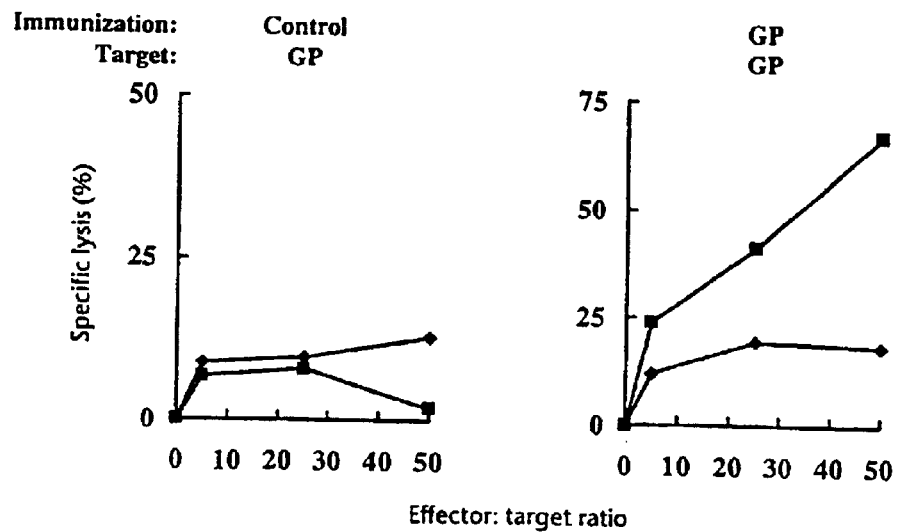

FIG. 2C. Mice immunized with GP were analyzed for their ability to lyse a syngeneic CT26 cell stably expressing GP or CT26 vector control transduced line at the indicated E/T ratios.

Figure 2D:
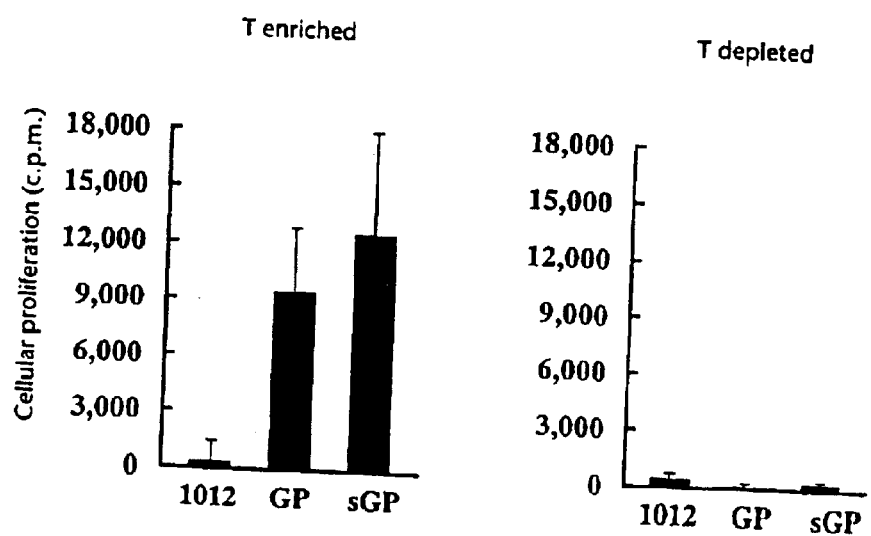

FIG. 2D. Cellular proliferative response in the indicated immunized mice. T cells, enriched or depleted (see, Specific Example, II. Methods), were incubated at $10^5$ cells/ml with sGP condition media (25%). Background was determined with cells incubated in media from control transfected 293 cells and subtracted from proliferation seen in sGP-containing supernatants.

Figure 3A:
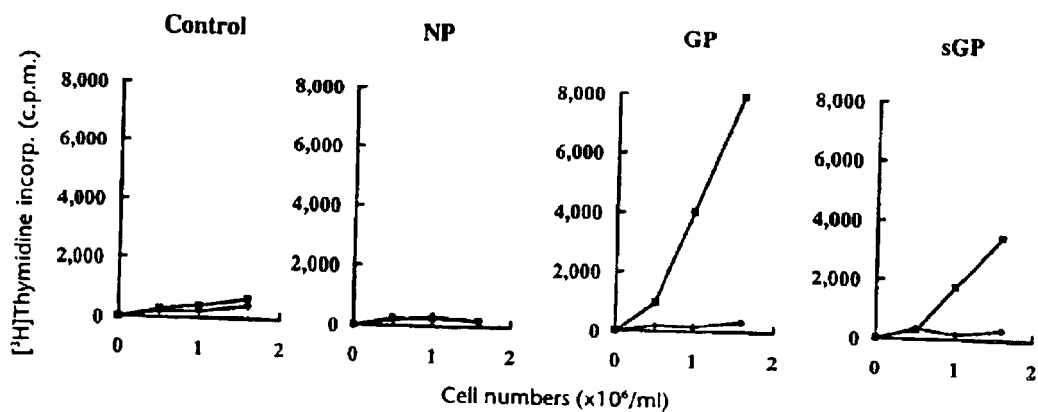
Figure 3B:
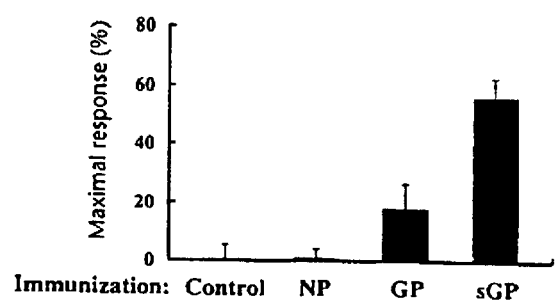
Figure 3C:
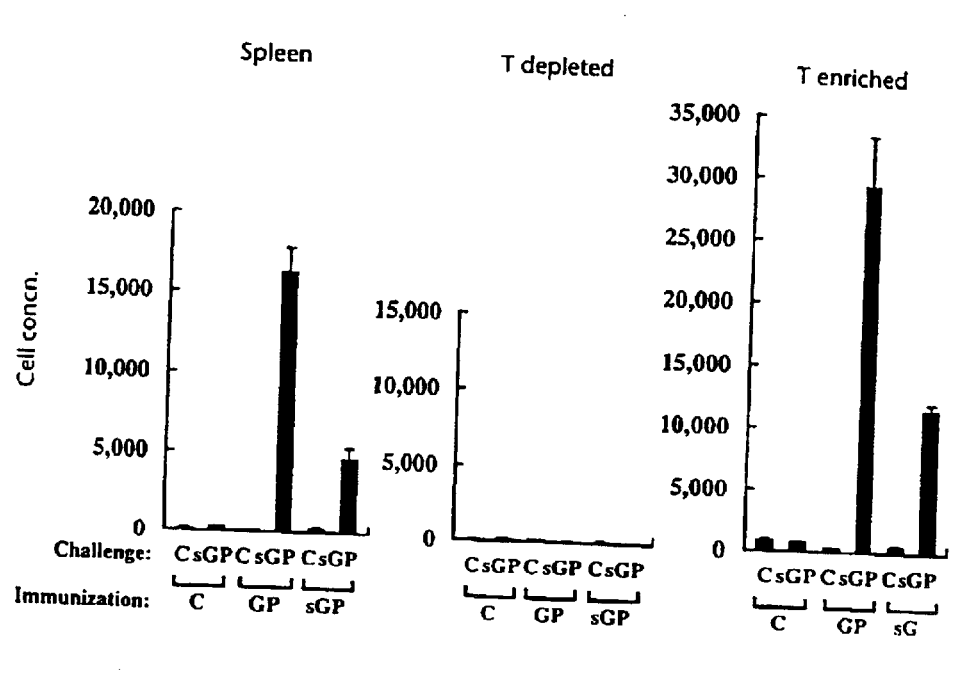
Figure 4A:
Figure 4C:
Figure 4E:
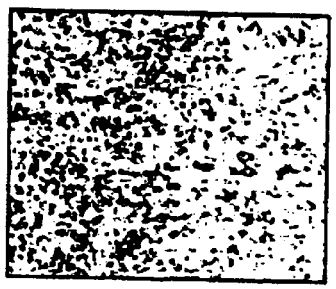
Figure 4B:
Figure 4D:
Figure 4F:

FIGS. 3A–3C are graphs showing immunization with sGP or GP expression plasmids induces T cell responses to sGP in guinea pigs.

FIGS. 3A–3C. Cell-mediated immunity in guinea pigs was analyzed by performing assays to detect cell proliferation to control or GP antigen (A) or T-cell growth factor production in response to the indicated antigens. The culture supernatants containing these antigens were prepared as previously described (Bottomly, K. et al., Measurement of human and murine interleukin 2 and interleukin 4. in *Current Protocols in Immunology*. (eds., Coligan, J. E. Kruisbeek, A. M., Margulies, D. H., Shevach, E. M.& Strober, W.) 6.3.1–6.3.12 (New York, John Wiley & Sons, Inc. 1992); Arai, H. et al., *Nat. Med.* 3:843–848 (1997)), and included at a final concentration of 10% (volume/volume). In A, cell numbers refer to the concentration of spleen cells per ml in the $^3$H-thymidine proliferation assay. In B, supernatants from A, harvested at the time of the peak proliferative response to sGP, were incubated with primary guinea pig T cells maintained in 200 U/ml of human IL-2. The percent maximal response refers to the magnitude of stimulation in response to the indicated stimuli relative to supernatants from 24 hour concanaval (in A-stimulated cells (2 µg/ml)). The requirement of T lymphocytes in guinea pig spleen cells for the proliferative response to sGP, performed as described in Specific Example, II. Methods, is shown (C).

FIGS. 4A–4F are photographs showing the immunohistochemical analysis of Ebola virus antigens in liver, lung, and spleen from representative protected (GP-animal 3) or infected (vector-animal 2) guinea pigs.

FIGS. 4A–4F. Magnification: liver, 40×; lung, 20×; spleen, 20×.

Figure 5:
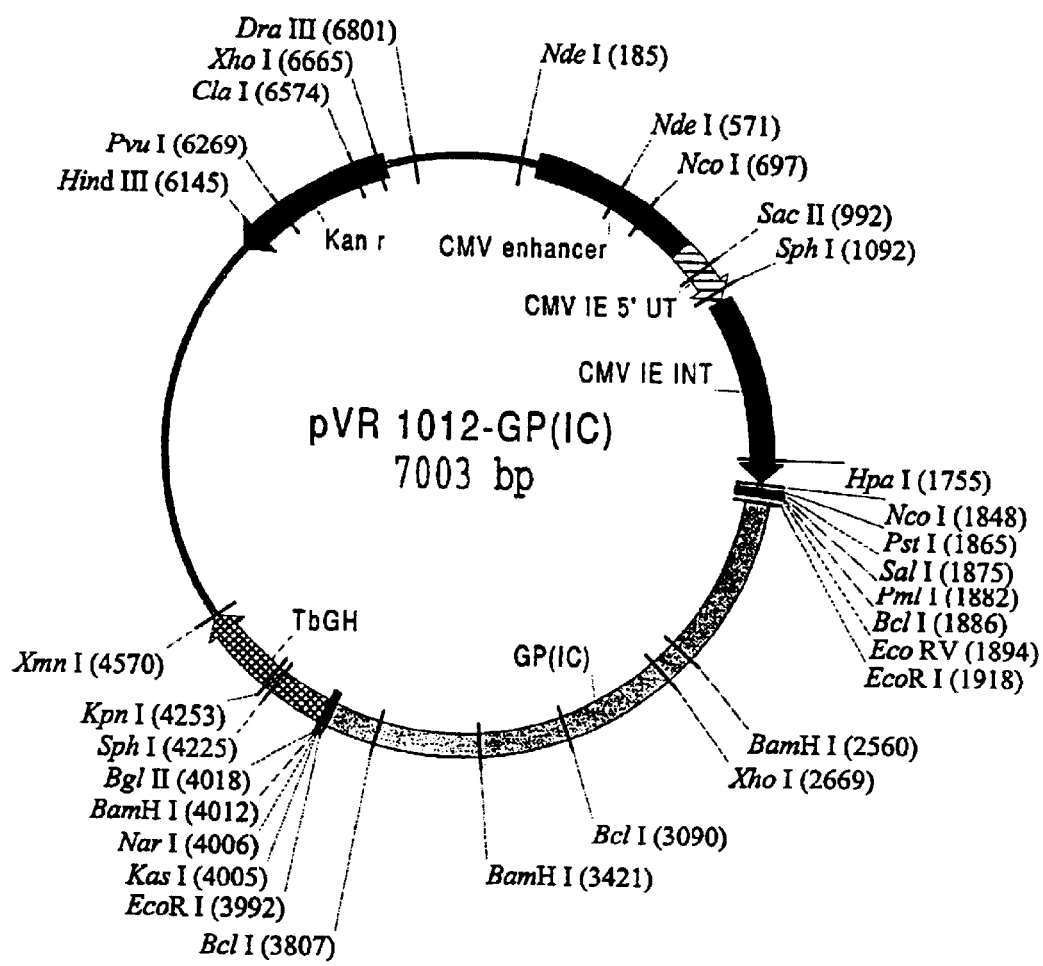

FIG. 5 is a schematic of the plasmid pVR 1012-GP(IC) (Ivory Coast strain of GP, SEQ ID NO: 1).

Figure 6:
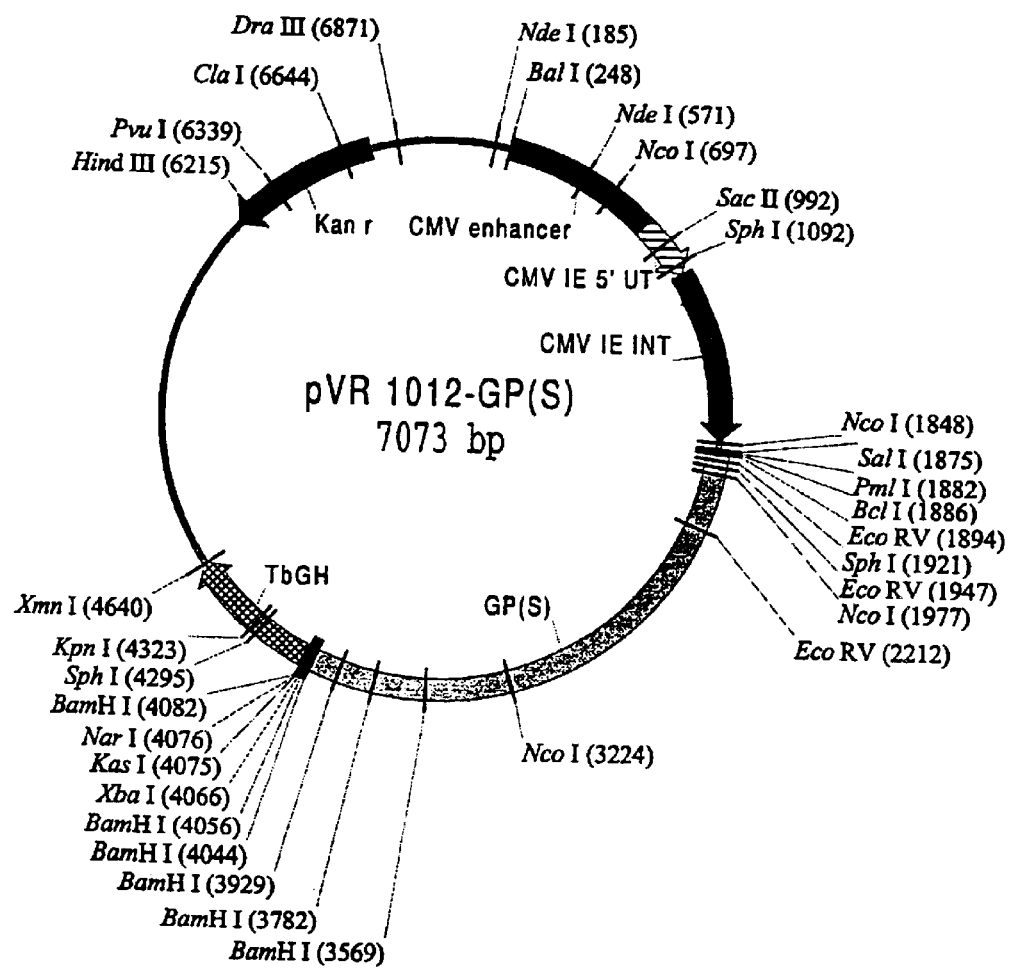

FIG. 6 is a schematic of the plasmid pVR 1012-GP(S) (Sudan strain of GP, see SEQ ID NO: 2).

Figure 7:
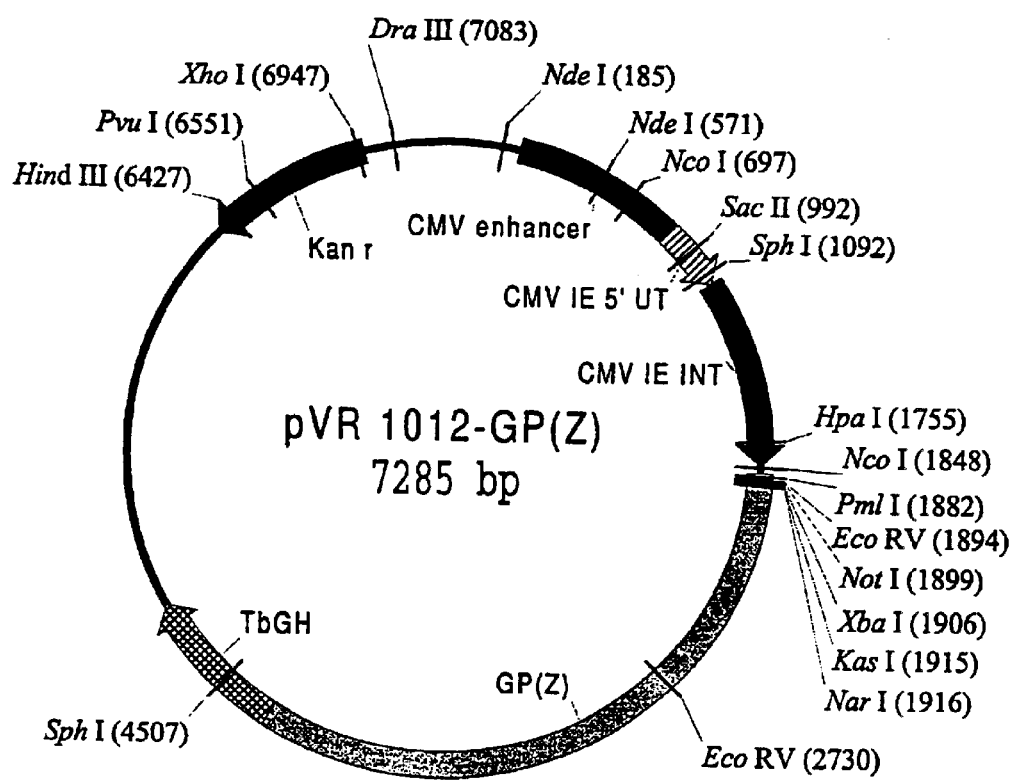

FIG. 7 is a schematic of the plasmid pVR 1012-GP(Z) (Zaire strain of GP, see SEQ ID NO: 3).

Figure 8:
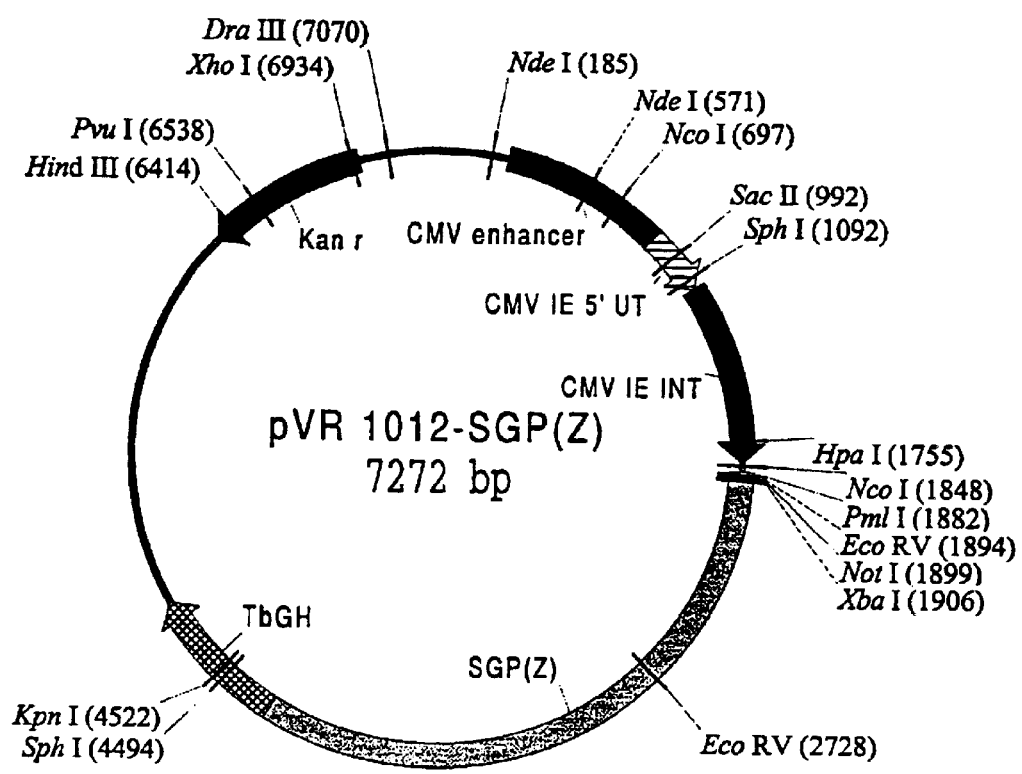

FIG. 8 is a schematic of the plasmid pVR 1012-sGP(Z) (Zaire strain of sGP, see SEQ ID NO: 4).

Figure 9:
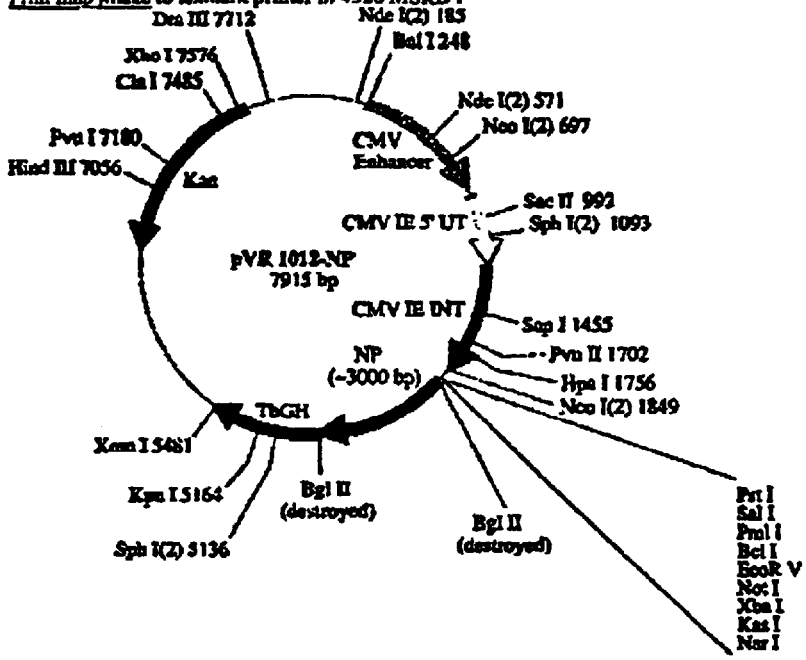

FIG. 9 is a schematic of the plasmid pVR 1012-NP.

DETAILED DESCRIPTION OF THE PREFERRED EMBODIMENTS

Ebola virus vaccines are provided comprising a nucleic acid molecule encoding an Ebola viral protein operatively-linked to a control sequence in a pharmaceutically acceptable carrier. In one embodiment, the nucleic acid molecule encodes the transmembrane form of the viral glycoprotein (GP). In another embodiment, the nucleic acid molecule encodes the secreted form of the viral glycoprotein (sGP). In yet another embodiment, the nucleic acid molecule encodes the viral nucleoprotein (NP).

The present invention further includes vaccines comprising nucleic acid molecules encoding Ebola viral proteins other than GP, sGP, and NP, e.g., other structural gene products which elicit protective immunity from disease caused by infection with Ebola virus. The nucleic acid molecules of the vaccines of the present invention encode structural gene products of any Ebola viral strain including the Zaire, Sudan, Ivory Coast and Reston strains. Nucleic acid molecules encoding structural gene products of the genetically-related Marburg virus strains may also be employed. Moreover, the nucleic acid molecules of the present invention may be modified, e.g., the nucleic acid molecules set forth herein may be mutated, as long as the modified expressed protein elicits protective immunity from disease caused by infection with Ebola virus. For example, the nucleic acid molecule may be mutated so that the expressed protein is less toxic to cells. The present invention also includes vaccines comprising a combination of nucleic acid molecules. For example, and without limitation, nucleic acid molecules encoding GP, sGP and NP of the Zaire, Sudan and Ivory Coast Ebola strains may be combined in any combination, in one vaccine composition.

The present invention also provides methods for immunizing a subject against disease caused by infection with Ebola virus comprising administering to the subject an immunoeffective amount of an Ebola virus vaccine. Methods of making and using Ebola virus vaccines are also provided by the present invention including the preparation of pharmaceutical compositions.

As referred to herein, the tern "encoding" is intended to mean that the subject nucleic acid may be transcribed in a cell, e.g., when the subject nucleic acid is linked to appropriate control sequences such as a promoter in a suitable vector (e.g., an expression vector) and the vector is introduced into a cell. The nucleic acid molecules of the present invention may be DNA molecules, cDNA molecules or RNA molecules, and are preferably cDNA molecules. The term "operatively-linked" as used herein refers to functional linkage between a nucleic acid expression control sequence (such as a promoter) and a second nucleic acid sequence, wherein the expression control sequence directs transcription of the nucleic acid corresponding to the second sequence. Expression control sequences are known to those skilled in the art (see, e.g., Goeddel, *Gene Expression Technology: Methods in Enzymology* 185, Academic Press, San Diego, Calif. (1990)). Vectors which contain both a promoter and a cloning site to which an inserted piece of nucleic acid is operatively-linked to the promoter, are well known in the art and are generally referred to herein as "expression vectors" or "expression vector plasmids". Preferably, these vectors are capable of transcribing nucleic acid in vitro and in vivo. A preferred vector is the *cytomegalovirus* (CMV) expression vector which directs high levels of gene expression in muscle.

Nucleic acid molecules which hybridize under stringent conditions to the nucleic acid molecules described herein are also within the scope of the present invention. As will be appreciated by those skilled in the art, multiple factors are considered in determining the stringency of hybridization including species of nucleic acid, length of nucleic acid probe, $T_m$ (melting temperature), temperature of hybridization and washes, salt concentration in the hybridization and wash buffers, aqueous or formamide hybridization buffer, and length of time for hybridization and for washes. An example of stringent conditions are DNA—DNA hybridization with a probe greater than 200 nucleotides in 5×SSC, at 65° C. in aqueous solution or 42° C. in formamide, followed by washing with 0.1×SSC, at 65° C. in aqueous solution. (Other experimental conditions for controlling stringency are described in Maniatis, T. et al., *Molecular Cloning: a Laboratory Manual*, Cold Springs Harbor Laboratory, Cold Springs, N.Y. (1982) at pages 387–389 and Sambrook, J. et al., *Molecular Cloning: a Laboratory Manual*, Second Edition, Volume 2, Cold Springs Harbor Laboratory, Cold Springs, N.Y., at pages 8.46–8.47 (1989)).

It will be appreciated that administration of the vaccines of the present invention can be by any of the routes normally used for gene therapy. In a preferred method, administration is by Intramuscular injection, however, other procedures for transfecting cells may also be employed, such as transfection using calcium phosphate coprecipitation, liposome-mediated transfection, plasmid and viral vector-mediated transfection and DNA protein complex-mediated transfection. Viral vector-mediated transfection includes, without limitation, the use of retroviral, replication-deficient retroviral, adenoviral and adeno-associated viral vectors. Cells transfected by the vaccines in the context of ex vivo gene therapy can also be administered.

It will be appreciated that more than one route of administering the vaccines of the present invention may be employed either simultaneously or sequentially (e.g., boosting). In addition, the vaccines of the present invention may be employed in combination with traditional immunization approaches such as employing protein antigens, vaccinia virus and inactivated virus, as vaccines. Thus, in one embodiment, the vaccines of the present invention are administered to a subject (the subject is "primed" with a vaccine of the present invention) and then a traditional vaccine is administered (the subject is "boosted" with a traditional vaccine). In another embodiment, a traditional vaccine is first administered to the subject followed by administration of a vaccine of the present invention. In yet another embodiment, a traditional vaccine and a vaccine of the present invention are co-administered.

Immunogenicity may be significantly improved if the vaccines of the present invention are co-administered with an immunostimulatory agent or adjuvant. Adjuvants enhance immunogenicity but are not necessarily immunogenic themselves. Immunostimulatory agents or adjuvants have been used for many years to improve the host immune responses to, for example, vaccines. Adjuvants may thus be employed to enhance the immunogenicity of the vaccines of the present invention, as well as the immunogenicity of traditional vaccines. Suitable adjuvants are well known to those skilled in the art and include, without limitation, aluminum phosphate, aluminum hydroxide, QS21, Quil A, derivatives and components thereof, calcium phosphate, calcium hydroxide, zinc hydroxide, a glycolipid analog, an octodecyl ester of an amino acid, a muramyl dipeptide, polyphosphazene, a lipoprotein, ISCOM matrix, DC-Chol, DDA, and other adjuvants and bacterial toxins, components and derivatives thereof.

The vaccines of the present invention may also be co-administered with cytokines to further enhance immunogenicity. The cytokines may be administered by methods known to those skilled in the art, e.g., as a nucleic acid molecule in plasmid form or as a protein or fusion protein.

Upon inoculation with a pharmaceutical composition as described herein, the immune system of the host responds to the vaccine by producing antibodies, both secretory and serum, specific for Ebola virus proteins. As a result of the vaccination, the host becomes at least partially or completely immune to Ebola virus infection, or resistant to developing moderate or severe disease caused by Ebola virus infection. Although Ebola virus infection and disease caused thereby are discussed in detail herein, it will be appreciated that the vaccines and methods of the present invention may be employed to immunize a subject against hemorrhagic fever generally, such as that caused by infection by the genetically-related Marburg virus.

Pharmaceutical compositions comprising the nucleic acid molecules encoding Ebola viral proteins described herein, either alone or in combination, and a pharmaceutically acceptable carrier, are also provided by the present invention. As used herein, the phrase "pharmaceutically acceptable carrier" encompasses any of the standard pharmaceutical carriers, such as those suitable for parenteral administration, such as, for example, by intramuscular, intraarticular (in the joints), intravenous, intradermal, intraperitoneal, and subcutaneous routes. Examples of such formulations include aqueous and non-aqueous, isotonic sterile injection solutions, which contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations suitable for oral administration can consist of (a) liquid solutions, such as an effective amount of the vaccine dissolved in diluents, such as water, saline or PEG 400; (b) capsules, sachets or tablets, each containing a predetermined amount of the vaccine, as liquids, solids, granules or gelatin; (c) suspensions in an appropriate liquid; (d) suitable emulsions; and (e) polysaccharide polymers such as chitians. The vaccine, alone or in combination with other suitable components, may also be made into aerosol formulations to be administered via inhalation, e.g., to the bronchial passageways. Aerosol formulations can be placed into pressurized acceptable propellants, such as dichlorodifluoromethane, propane, nitrogen, and the like.

Suitable formulations for rectal administration include, for example, suppositories, which consist of the vaccine with a suppository base. Suitable suppository bases include natural or synthetic triglycerides or paraffin hydrocarbons. In addition, it is also possible to use gelatin rectal capsules which consist of a combination of the vaccine with a base, including, for example, liquid triglycerides, polyethylene glycols, and paraffin hydrocarbons.

Each carrier must be "acceptable" in the sense of being compatible with the other ingredients of the formulation and not injurious to the recipient, e.g., the patient. The formulations can be presented in unit-dose or multi-dose sealed containers, such as ampules or vials and may be prepared by any method known in the art.

Pharmaceutical compositions comprising any of the nucleic acid molecules encoding Ebola viral proteins of the present invention are useful to immunize a subject against disease caused by Ebola virus infection. Thus, this invention further provides methods of immunizing a subject against disease caused by Ebola virus infection, e.g., hemorrhagic fever, comprising administering to the subject an immunoeffective amount of a pharmaceutical composition of the invention. This subject may be an animal, for example a mammal, such as a primate or preferably a human.

The vaccines of the present invention are also suitable for veterinary immunization. The vaccines of the present invention comprising nucleic add molecules encoding Ebola virus structural gene products from the Reston strain, which is known to infect animals, are particularly useful in such veterinary immunization methods.

The vaccines are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner and may be monitored on a patient-by-patient basis. However, suitable dosage ranges are readily determinable by one skilled in the art and generally range from about 300 $\mu$g to about 4–5 mg. The dosage may also depend, without limitation, on the route of administration, the patient's state of health and weight, and the nature of the formulation.

Methods of immunizing a subject against multiple strains of Ebola virus are further provided herein. The nucleic acid molecules encoding Ebola viral proteins of the present invention may be combined with nucleic acid molecules encoding other viral proteins of other virus strains to achieve protection against multiple strains of Ebola virus. Typically the vaccines will be in an admixture and administered simultaneously, but may also be administered separately.

In some instances it may be desirable to combine the Ebola virus vaccines of the present invention with vaccines which induce protective responses to other agents, particularly other viruses. For example, the vaccine compositions of the present invention can be administered simultaneously, separately or sequentially with other genetic immunization vaccines such as those for influenza (Ulmer, J. B. et al., *Science* 259:1745–1749 (1993); Raz, E. et al., *PNAS (USA)* 91:9519–9523 (1994)), malaria (Doolan, D. L. et al., J. Exp. Med. 183:1739–1746 (1996); Sedegah, M. et al., *PNAS (USA)* 91:9866–9870 (1994)), and tuberculosis (Tascon, R. C. et al., *Nat. Med.* 2:885–892 (1996)).

It will also be appreciated that single or multiple administrations of the vaccine compositions of the present invention may be carried out. For example, subjects who are particularly susceptible to Ebola virus infection may require multiple immunizations to establish and/or maintain protective immune responses. Levels of induced immunity can be monitored by measuring amounts of neutralizing secretory and serum antibodies, and dosages adjusted or vaccinations repeated as necessary to maintain desired levels of protection.

This invention also provides kits comprising the vaccines of the present invention. For example, kits comprising a vaccine and instructions for use are within the scope of this invention.

The vaccines and methods of the present invention evoke a protective immune response and do not lead to immunopotentiation or exacerbated disease. The vaccines lack transmissibility, are genetically stable and induce protective levels of humoral and cell-mediated immunity.

In order to more fully demonstrate the advantages arising from the present invention, the following example is set forth. It is to be understood that the following is by way of example only and is not intended as a limitation on the scope of the invention.

SPECIFIC EXAMPLE

I. Results

Immune response to viral gene products in mice. To characterize immune responses to selected Ebola virus proteins, eukaryotic expression vector plasmids were injected into mice. The cytomegalovirus (CMV) immediate early region 1 enhancer was used to stimulate transcription because it directs high levels of gene expression in muscle. Manthorpe, M. et al., *Hum. Gene. Ther.* 4:419–431 (1993). cDNAs encoding an abundant structural protein, the major viral nucleocapsid phosphoprotein (NP), the secreted glycoprotein (sGP), or the membrane-associated glycoprotein (GP) were inserted. Alternative forms of GP were chosen because it had been postulated that the transmembrane protein contained a protein sequence motif also found in oncogenic retroviruses that might suppress immune responses.

Burkreyev, A. A. et al., *FEBS. Lett.* 323:183–187 (1993); Cianciolo, G. J. et al., *Science* 230:453455 (1985); Harris, D. T. et al., *J. Immunol.* 138:889–894 (1987); Volchkov, V. E. et al., *FEBS. Lett.* 305:181–184 (1992); Sanchez, A. et al., *Virus. Res.* 29:215–240 (1993). Expression of the relevant proteins was confirmed after transfection of the human renal epithelial cell line, 293, by immunoblotting with antisera to these gene products (FIG. 1A). For NP, the expected full-length 104 kDa protein normally produced by the virus was seen, together with lower molecular weight species likely generated from truncated protein or degradation products described previously. Sanchez, A. et al., *Virology* 170:81–91 (1989). Similarly, expression of sGP and GP revealed a heterogeneous pattern whose sizes correlated with the expected products of cleavage or post-translational carbohydrate modification. Sanchez, A. et al., *PNAS (USA)* 93:3602–3607 (1996).

These plasmids were injected into mice to characterize their ability to induce humoral and cellular immune responses to the relevant viral proteins. Three injections, each with 50 $\mu$g of plasmid DNA in saline (100 $\mu$l), were performed at two-week intervals in Balb/C female mice (68 week old, Charles River). Serum from immunized recipients were examined for antibody responses. An antibody response to the viral NP gene product was readily detectable (FIG. 1B), with titers of $\geq$1:16,000 by Western blot analysis. The titer of antibody induced in response to injection with plasmids encoding the viral glycoproteins was lower. After immunization with GP, no antibody was detectable by Western blotting, while immunization with sGP induced an antibody response (FIG. 1B). The more sensitive ELISA (Ksiazek, T. G., *Lab. Anim.* 20:3446 (1991); Ksiazek, T. G. et al., *J. Clin. Microbiol.* 30:947–950 (1992)) did allow detection of antibodies to both GP and sGP at titers of 1:400 and 1:1,200, respectively. Cytolytic T cell (CTL) responses to these viral proteins were analyzed next. Despite the substantial humoral immune response to NP, minimal CTL activity was detected against syngeneic cells expressing this viral protein (FIG. 2A). In contrast, genetic immunization with sGP, which elicited a weaker antibody response, induced a marked cytolytic T cell response to cells expressing GP (FIG. 2B). Immunization with the GP plasmid also induced a significant CTL response to GP (FIG. 2C). These data suggested that both the secreted and transmembrane form of the protein could be processed for antigen presentation and the transmembrane form was a target for recognition by these cytolytic T cells. Finally, antigen-specific T cell proliferation to sGP was also observed in GP and sGP but not plasmid control injected mice (FIG. 2D).

The ability of antibodies detected in mouse sera after immunization to neutralize virus was tested in an in vitro infection assay. McCormick, J. B. et al., *J. Infect. Dis.* 147:264–267 (1983). In no case was neutralization of infectivity observed, even at titers of 1:10 (data not shown), despite the documented presence of antibody after NP and sGP immunization by Western blot analysis. Infectivity in vitro was thus not inhibited by Ebola-specific antibodies.

Immune function and viral challenge in guinea pigs. To determine whether the in vivo immune responses could protect against viral infection, virus was adapted to grow in guinea pigs. Though this species is not well-suited to analysis of immune function, infection in adult mice has not been successful. Moreover, infection in guinea pigs, used originally to propagate virus from infected humans, is a well-established animal model for the human disease. Infection gives rise to a syndrome of hemorrhagic fever with levels of virus, organ pathology, and infection of reticuloendothelial and mononuclear cells comparable to humans. Bowen, E. T. W. et al., *Lancet* 1:571–573 (1977).

Two groups of immunized guinea pigs were studied. Animals were injected intramuscularly with the relevant expression vector plasmids, and the response to infection in groups immunized with either sGP, GP, NP, or control plasmids was observed. In the first group, animals were challenged within 2 months after the initial immunization, at which time the antibody titers were high, ranging from 1:1,600 to >1:25,000 (Table 1A). In these animals, nearly complete protection from lethal challenge was observed in GP (%), sGP (5/5), and NP (4/4) immunized subjects, in contrast to controls (0/6). In a second group, guinea pigs were challenged four months after the initial immunization (Table 1B). As in the first group, all animals immunized with the control vector succumbed to infection within a week after virus challenge (n=4). In this group, antibody titers were lower, and three of the four guinea pigs immunized with NP succumbed to infection, with the single survivor appearing severely ill after 1 week, in contrast to the protective response with NP at the earlier time point after immunization in Group I. More effective protection was seen in animals immunized with vector expressing GP, protection was noted in four of five animals challenged, with one survivor appearing weak but surviving the viral challenge. Similarly, three of the five animals immunized with sGP showed no ill effects following viral challenge. Protection in this group again correlated with the ability to sustain an effective immune response to GP or sGP. Together, all guinea pigs immunized with vectors expressing GP or sGP which had titers greater than 1:5,120 were resistant to infection (11/11) compared to 0/10 controls (p=0, by Fisher's exact test). Twelve of fourteen animals with antibody titers ≧2,560 survived viral challenge compared to controls (p=0.00003, by Fisher's exact test). Similar to immunized mice, guinea pigs injected with GP or sGP plasmids were able to generate cell-mediated immune responses to the viral glycoprotein in addition to the antibody response. These responses were antigen-specific and T cell-dependent, as detected in sGP antigen-dependent spleen cell proliferation and T-cell growth factor assays (FIGS. 3A–C). Thus, the ability to generate and sustain significant cellular immune responses in vivo correlated with protection from infection. Though antibody titer correlated with protection, cell-mediated immunity appeared necessary for protection since passive transfer of antibody to GP does not confer protection (Peters, C. J. et al., *Filoviridae*: Marburg and Ebola Viruses. in *Fields Virology*. (eds., Fields, B. N., Knipe, D. M.& Howley, P. M.) 1161–1176 (Philadelphia, Lippincott-Raven, 1996); Jahrling, P. B. et al., *Arch. Virol. Suppl.* 11:135–140 (1996)) and antisera from protected guinea pigs did not inhibit virus replication in vivo (n=3) or at a 1:10 dilution in vitro (data not shown). Since the Hartley guinea pig to which the virus has been adapted for growth is outbred, cellular adoptive transfer studies could not be performed.

TABLE 1

| Plasmid | Subject | ELISA(Pre) | ELISA(Post) | Viral Ag | Survival |
|---|---|---|---|---|---|
| Group I | | | | | |
| GP | 1 | >1:25,600 | 1:12,800 | – | Yes |
| GP | 2 | >1:25,600 | 1:25,600 | – | Yes |
| GP | 3 | >1:25,600 | 1:25,600 | – | Yes |
| GP | 4 | 1:25,600 | 1:6,400 | – | Yes |
| GP | 5 | 1:25,600 | 1:12,800 | – | Yes |
| GP | 6 | 1:25,600 | 1:25,600 | – | Yes |
| SGP | 1 | 1:12,800 | 1:25,600 | – | Yes |
| SGP | 2 | 1:6,400 | 1:25,600 | – | Yes |
| SGP | 3 | 1:6,400 | 1:25,600 | – | Yes |
| SGP | 4 | 1:25,600 | 1:25,600 | – | Yes |
| SGP | 5 | >1:25,600 | 1:12,800 | – | Yes |
| SGP | 6 | 1:1,600 | Negative | + | No |
| NP | 1 | 1:12,800 | >1:25,600 | – | Yes |
| NP | 2 | >1:25,600 | 1:25,600 | – | Yes |
| NP | 3 | 1:12,800 | 1:12,800 | – | Yes |
| NP | 4 | 1:25,600 | 1:25,600 | – | Yes |
| Vector alone | 1 | Negative | Negative | + | No |
| Vector alone | 2 | Negative | n.d. | + | No |
| Vector alone | 3 | Negative | Negative | + | No |
| Vector alone | 4 | Negative | Negative | + | No |
| Vector alone | 5 | Negative | n.d. | + | No |
| Vector alone | 6 | Negative | n.d. | + | No |

Guinea pigs were immunized on days 1, 14, 28, 42, and challenged on day 62.

| | | Group II | | | |
|---|---|---|---|---|---|
| GP | 1 | 1:2,560 | n.d. | +/f | No |
| GP | 2 | 1:5,120 | 1:10,240 | – | Yes |
| GP | 3 | 1:10,240 | 1:10,240 | – | Yes |
| GP | 4 | 1:1,280 | n.d. | +/f | No |
| GP | 5 | 1:5,120 | 1:20,480 | – | Yes (ill) |
| SGP | 1 | 1:2,560 | n.d. | + | No |
| SGP | 2 | 1:10,240 | 1:5,120 | +/f | Yes |
| SGP | 3 | 1:10,240 | 1:81,920 | – | Yes |
| SGP | 4 | 1:2,560 | 1:5,120 | – | Yes |
| SGP | 5 | 1:640 | n.d. | + | No |
| NP | 1 | n.d. | n.d. | + | No |
| NP | 2 | n.d. | n.d. | + | No |
| NP | 3 | n.d. | n.d. | + | No |
| NP | 4 | n.d. | Negative | + | Yes (ill) |
| Vector alone | 1 | Negative | n.d. | + | No |
| Vector alone | 2 | Negative | n.d. | + | No |
| Vector alone | 3 | Negative | n.d. | + | No |
| Vector alone | 4 | Negative | n.d. | + | No |

Guinea pigs were immunized on days 1, 14, 42, and 112 and challenged on day 122.
n.d. = not done. Viral ag denotes presence of virus determined by immunohistochemistry (30) performed on spleen, liver, lung, kidney, and heart tissues;
"+" = widespread systemic involvement of the mononuclear phagocyte system and to a lesser extent endothelial and parenchymal cells;
"+/f" = focal involvement (seen in the spleen of SGP #2, the liver and spleen of GP #1, and the lung of GP#4) where rare sites of anti-Ebola antibody staining were detected.;
"–" = no Ebola virus antigen detected in tissues.
ELISA determinations made prior to viral challenge (Pre) or at least 7 days after (Post) infection, respectively.
The surviving NP immunized animal (4) was found to have significant levels of virus in major organs by immunohistochemistry, and more than 5 logs of virus was detected in the serum and spleen, in contrast to GP and sGP animals where no virus was detected.

Histopathologic analysis of infection in immunized guinea pigs. Pathologic analysis revealed widespread issue necrosis and dissemination of virus by immunohistochemistry, similar to human disease. Virus load correlated with susceptibility to infection with titers of $\geq 10^5$ in infected animals compared to undetectable levels in immunized survivors. In infected animals, the liver, lung, and spleen showed evidence of significant viral antigen by immunohistochemistry (FIG. 4, Table 1), and both reticuloendothelial and mononuclear phagotic involvement was observed.

Determination of antibody response in animals which survived virus challenge revealed increases in the immune response to viral proteins when initial titers were lower (Table 1). Less consistent increases in antibody titers were observed in the NP immunized animals. These data suggest that Ebola virus infection may stimulate immunity in survivors of a viral challenge when immune responses are not optimal.

II. Methods

Plasmids. Plasmids containing the GP, sGP, or NP cDNAs (Sanchez, A. et al., *Virus. Res.* 29:215–240 (1993), Genbank) were used to subclone the relevant inserts into CMV expression vectors which utilized the bovine growth hormone polyadenylation sequence. Manthorpe, M. et al., *Hum. Gene. Ther.* 4:419–431 (1993). (see FIGS. 5–9 and SEQ ID NOS: 1–4). Briefly, for GP, plasmid pGEM-3Zf(-)-GP was digested with EcoR I, treated with the Klenow fragment of *E. coli* DNA polymerase, and digested with BamH I. The GP fragment was then inserted into the pCMV expression vector plasmid digested with BamH I, Klenow fragment and Bgl II. For sGP, the plasmid pCRII-sGP was digested with EcoR I, treated with Klenow enzyme, and the resulting fragment inserted into the BamH I/Bgl II CMV plasmid which had been incubated with Klenow fragment, calf intestinal phosphatase (CIP), then phenol chloroform extract. For the NP expression vector, plasmid pSP64—NP2 (Sanchez, A. et al., *Virology* 170:81–91 (1989)) was digested with EcoR I, treated with Klenow enzyme, and digested with BamH I. The NP insert was cloned into CMV treated with BamH I, Klenow enzyme, followed by heat inactivation and Bgl II digestion.

Cell lines and transfectants. For stable transfectants, the relevant cDNAs were inserted into a CMV expression plasmid containing a neomycin resistant gene, pCMV-neo (H. Arai, unpublished data), which was digested with Xba I, and treated with CIP and Klenow enzyme. The EcoR I/BamH I GP fragment from pGEM-3Zf(-)-GP, the EcoR I sGP fragment from pCRII-SGP, or the EcoR I/BamH I NP fragment from pSP64—NP2 was treated with Klenow enzyme and ligated to this plasmid backbone. These vectors were transfected into Renca or CT26 which was syngeneic to Balb/C mice using calcium phosphate and selected in 0.7 or 1 mg/ml G418 for 26 weeks. Expression of GP, sGP, or NP from these vectors in Renca or CT26 cells was also confirmed by Western blot analysis (data not shown).

Cell proliferation assay. Spleen cells from male Hartley guinea pigs or Balb/C female mice (8–10 weeks) immunized with the indicated plasmid expression vectors were incubated with sGP or vector control supernatants (25% volume:volume) from transfected 293 cells at the indicated cell concentrations. T cell depletion was performed using the CT5 monoclonal antibody (Tan, B. T. G. et al., *Hybridoma* 4:115–124 (1985)) (Biosource, Camarillo, Calif.) for guinea pigs or anti-Thy 1.2 antibody in the mouse using immunomagnetic microbeads (Miltenyi Biotec, Inc., Auburn, Calif.).

Viral challenge in guinea pigs. Animals were immunized by injection of 100 µl (0.5 mg/ml) in each hind leg (two injections at each time point) with the indicated plasmid expression vectors. Animals were challenged by inoculation with a stock of Ebola virus (Zaire, 1976) that had been passaged once in vero E6 cells and serially passaged by intraperitoneal injection of spleen homogenates in Hartley guinea pigs seven times. Immunized guinea pigs were injected intraperitoneally with 0.5 ml of a 1:1,000 dilution of spleen cell homogenate in Hank's balanced salt solution 122 days after the initial plasmid DNA injection (1000 pfu). Survival was determined 10 days later at which times animals were sacrificed for serologic and pathologic analysis. ELISA, enzyme-linked immunosorbent assay (Volchkov, V. E. et al., *FEBS. Left.* 305:181–184 (1992); Sanchez, A. et al., *Virus. Res.* 29:215–240 (1993)) on infected cell supernatants and enriched viral extracts containing GP, sGP, or NP were performed as previously described.

III. Discussion

Following the initial report that injection of plasmid DNA into muscle could direct the synthesis of recombinant proteins (Wolff, J. A. et al., Science 247:1465–1468 (1990)), the suggestion was made that this gene transfer approach may be useful for vaccination and was termed genetic immunization. Tang, D. C. et al., *Nature* 356:152–154 (1992). This approach has been applied to different infectious diseases, including influenza (Ulmer, J. B. et al., *Science* 259:1745–1749 (1993); Raz, E. et al., *PNAS (USA)* 91:9519–9523 (1994)), malaria (Doolan, D. L. et al., *J. Exp. Med.* 183:1739–1746 (1996); Sedegah, M. et al., *PNAS (USA)* 91:9866–9870 (1994)), and tuberculosis (Tascon, R. C. et al., *Nat. Med.* 2:888–892 (1996)) and has also been used to modulate antibody and cell-mediated immune responses in autoimmune and allergic diseases. Raz, E. et al., *PNAS (USA)* 90:4523–4527 (1993); Waisman, A. et al., *Nat. Med.* 2:899–905 (1996); McCormick, J. B. et al., *J. Infect. Dis.* 147:264–267 (1983); Border, W. A. et al., *Nat. Med.* 1:1000–1001 (1995).

The immune response to selected Ebola virus proteins after genetic immunization in mice was analyzed and their ability to protect against lethal infection in a susceptible animal model, the guinea pig, was tested. The immune analyses performed in different species suggest similar patterns of response, though the specific peptides which may be recognized by the immune system to confer protection in the guinea pig could differ from the mouse. Because the principles of MHC antigen presentation and recognition apply broadly across species (Monaco, J. J., *Immunol. Today* 13:173–179 (1992); Jorgensen, J. L. et al., *Annu. Rev. Immunol.* 10:835–873 (1992); Zinkemagel, R. M. et al., *Immunol. Today* 18:14–17 (1997)), the finding that protection was observed in different members of an outbred strain and that similar immune responses were seen in different species is not unexpected and suggests that this approach may be applicable to humans.

Immunization with plasmids encoding distinct viral proteins induced different antibody and cytolytic T cell responses. The broadest immune response was conferred by GP and sGP, which induced both cellular and humoral immunity to the membrane-associated GP. In guinea pigs challenged with doses of virus that are otherwise lethal, sGP provided nearly equivalent protection to GP, with no significant difference between these groups. The ability of vectors expressing GP to confer immunity may be explained by the generation of lower molecular weight degradation products (FIG. 1B) which could provide sufficient protein for antigen presentation to induce detectable, cellular, and humoral immune responses in guinea pigs.

Despite the fact that plasmid DNA injection has been shown to affect the immune response to different antigens in infectious and autoimmune diseases, the ability of individual gene products to protect against disease in vivo is not readily predictable. In particular, the rapid rates of Ebola virus replication and the poor immunogenicity of its proteins had previously rendered it resistant to immune interventions. Several attempts to confer protection with passive transfer of immunoglobulin were unsuccessful (Peters, C. J. et al., *Filoviridae*: Marburg and Ebola Viruses. in *Fields Virology*. (eds., Fields, B. N., Knipe, D. M.& Howley, P. M.) 1161–1176 (Philadelphia, Lippincott-Raven, 1996); Jahrling, P. B. et al., *Arch. Virol. Suppl.* 11:135–140 (1996)), in agreement with the finding set forth herein that antisera from protected animals fails to neutralize virus replication in vitro. Previous studies using formalin-fixed virus or purified viral proteins for immunization have also not proven effective. Peters, C. J. et al., *Filoviridae*: Marburg and Ebola Viruses. in *Fields Virology*. (eds., Fields, B. N., Knipe, D. M.& Howley, P. M.) 1161–1176 (Philadelphia, Lippincott-Raven, 1996); Clegg. J. C. S. & Sanchez, A. Vaccines against arenaviruses and filoviruses. in *New Generation Vaccines*. (eds., Levine, M. M., Woodrow, G. C., Kaper, J. B.& Cobon, G. S.) 749–765 (New York, N.Y., Marcel Dekker, Inc. 1997).

It is likely that traditional immunization approaches using protein antigens, vaccinia virus, or inactivated virus do not allow for appropriate uptake and presentation of viral antigens by dendritic or other antigen-presenting cells to induce protective immune responses. It has been shown recently that genetic immunization leads to production of recombinant protein(s) in muscle which are delivered to bone marrow-derived antigen-presenting cells. Iwasaki, A. et al., *J. Immunol.* 159:11–14 (1997); Doe, B. et al., *PNAS* (*USA*) 93:8578–8583 (1996); Corr, M. et al., *J. Exp. Med.* 184:1555–1560 (1996). Synthesis of Ebola glycoprotein after gene transfer apparently allows more efficient processing and presentation and the generation of immune responses not seen with virus or with viral vectors. GP is a large molecule which contains both T and B cell epitopes. Although antibody levels provide a surrogate marker of protection, the fact that passive transfer of antibody did not confer protection implies that immunoglobulin switching and synthesis is reflective of the T helper response to GP. Genetic immunization stimulates T helper cells to generate both CTL and B cell antibody responses to the virus. Although antibody production confirms effective immunization, a productive T cell response, likely involving $T_H 1$ cell stimulation, as shown by the T cell proliferation and CTL assays (FIG. 3), is needed for effective immunity. Taken together, these studies suggest that transcription and translation of viral genes in host cells by genetic immunization induces alternative, more effective, processing and antigen presentation which better stimulates immunity to Ebola virus. Since there are yet no effective antiviral agents, the ability to generate protective immunity by vaccination may prove useful in selected high risk populations, particularly in regions of ongoing outbreaks, and among medical and laboratory personnel exposed to the virus. Although it remains important to identify agents which treat acute infection, genetic immunization may help to limit the spread of this highly lethal infectious disease.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All references cited herein are incorporated by reference as if fully set forth.

We claim:

1. A pharmaceutical composition comprising a nucleic acid molecule encoding an Ebola virus structural gene product operatively-linked to a heterologous control sequence, in a pharmaceutically acceptable carrier, wherein the Ebola virus structural gene product is the transmembrane form of the Ebola virus glycoprotein.

2. The pharmaceutical composition of claim 1, wherein the control sequence is a promoter.

3. The pharmaceutical composition of claim 2, wherein the promoter is the CMV immediate-early region 1 promoter.

4. The pharmaceutical composition of claim 1, further comprising an adjuvant.

5. A method of producing a vaccine against disease caused by infection by Ebola virus, comprising the steps of:
   a) administering the pharmaceutical composition of claim 1 to a test host to determine an amount and a frequency of administration thereof to elicit a protective immune response in said host; and
   b) formulating said pharmaceutical composition in a form suitable for administration to a treatable host in accordance with said determined amount and frequency of administration.

6. A vaccine comprising a nucleic acid molecule encoding the transmembrane form of the Ebola virus glycoprotein operatively-linked to a heterologous control sequence, in a pharmaceutically acceptable carrier.

7. The vaccine of claim 6, further comprising an adjuvant.

8. A method of immunizing a subject against hemorrhagic fever comprising the step of administering to the host an immunoeffective amount of the vaccine of any of claims 6 to 7, wherein the hemorrhagic fever is caused by infection with Ebola virus.

9. The method of claim 8, wherein the host is a human and administration is by intramuscular injection.

10. The method of claim 8, wherein the subject receives a second administration of an immunoeffective amount of a vaccine against disease caused by infection by Ebola virus.

11. The vaccine of claim 6, wherein the control sequence is a promoter.

12. The vaccine of claim 11, wherein the promoter is the CMV immediate-early region 1 promoter.

* * * * *